United States Patent
Moros

(10) Patent No.: US 8,314,115 B2
(45) Date of Patent: *Nov. 20, 2012

(54) METHOD OF TREATING MOVEMENT DISORDERS USING BARBITURIC ACID DERIVATIVES

(75) Inventor: Daniel A. Moros, Larchmont, NY (US)

(73) Assignee: Taro Pharmaceutical Industries Limited, Haifa Bay (IL)

( * ) Notice: Subject to any disclaimer, the term of this patent is extended or adjusted under 35 U.S.C. 154(b) by 394 days.

This patent is subject to a terminal disclaimer.

(21) Appl. No.: 12/638,227

(22) Filed: Dec. 15, 2009

(65) Prior Publication Data

US 2010/0311771 A1    Dec. 9, 2010

Related U.S. Application Data

(63) Continuation of application No. 11/355,339, filed on Feb. 16, 2006, now Pat. No. 7,776,871, which is a continuation of application No. 10/735,514, filed on Dec. 11, 2003, now Pat. No. 7,166,610.

(60) Provisional application No. 60/432,470, filed on Dec. 11, 2002.

(51) Int. Cl.
*A61K 31/515*    (2006.01)
*C07D 239/62*    (2006.01)
*C07D 239/64*    (2006.01)

(52) U.S. Cl. ..................................... 514/270

(58) Field of Classification Search .......... None
See application file for complete search history.

(56) References Cited

U.S. PATENT DOCUMENTS

| | | |
|---|---|---|
| 1,960,170 A | 5/1934 | Schnider |
| 2,119,701 A | 6/1938 | Callsen |
| 2,673,205 A | 3/1954 | Hoffmann et al. |
| 3,679,683 A | 7/1972 | Gorbaty |
| 3,711,607 A | 1/1973 | Vida et al. |
| 3,900,475 A | 8/1975 | Vida et al. |
| 3,904,627 A | 9/1975 | Vida et al. |
| 3,919,427 A | 11/1975 | Vida et al. |
| 3,930,006 A | 12/1975 | Wiggins et al. |
| 3,948,896 A | 4/1976 | Vida |
| 4,029,662 A | 6/1977 | Vida |
| 4,046,894 A | 9/1977 | Samour et al. |
| 4,060,528 A | 11/1977 | Janssen et al. |
| 4,260,769 A | 4/1981 | Stella et al. |
| 4,578,503 A | 3/1986 | Ishikawa et al. |
| 4,628,056 A | 12/1986 | Levitt et al. |
| 4,631,294 A | 12/1986 | Barsan |
| 4,833,148 A | 5/1989 | Olney |
| 4,894,459 A | 1/1990 | Bod et al. |
| 4,914,226 A | 4/1990 | Di Trapani et al. |
| 5,120,850 A | 6/1992 | Bod et al. |
| 5,128,477 A | 7/1992 | Bod et al. |
| 5,456,851 A | 10/1995 | Liu et al. |
| 5,474,990 A | 12/1995 | Olney |
| 5,750,766 A | 5/1998 | Krummel et al. |
| 5,756,815 A | 5/1998 | Knell |
| 5,808,066 A | 9/1998 | Krummel et al. |
| 5,985,856 A | 11/1999 | Stella et al. |
| 6,051,737 A | 4/2000 | Kim et al. |
| 6,093,820 A | 7/2000 | Gutman et al. |
| 6,156,925 A | 12/2000 | Meyer et al. |
| 6,184,238 B1 | 2/2001 | Takano et al. |
| 6,262,067 B1 | 7/2001 | Allen et al. |
| 6,281,207 B1 | 8/2001 | Richter et al. |
| 6,372,757 B1 | 4/2002 | Johns et al. |
| 6,638,528 B1 | 10/2003 | Kanios |
| 6,664,262 B2 | 12/2003 | Gutman et al. |
| 6,756,379 B2 | 6/2004 | Moros et al. |
| 6,906,079 B2 | 6/2005 | Gutman et al. |
| 6,939,873 B2 | 9/2005 | Gutman et al. |
| RE38,934 E | 1/2006 | Gutman et al. |
| 7,064,205 B2 | 6/2006 | Gutman et al. |

(Continued)

FOREIGN PATENT DOCUMENTS

CA    2158630 A1    3/1996

(Continued)

OTHER PUBLICATIONS

Silverman, "The Organic Chemistry of Drug Design and Drug Action" published 1992 by Academic Press, pp. 4-47, 352-397.*

(Continued)

*Primary Examiner* — Eric S Olson
(74) *Attorney, Agent, or Firm* — Venable LLP; Keith G. Haddaway; Michael E. Nelson

(57) ABSTRACT

A method of treating movement disorders comprises administering to a human or animal subject in need of treatment a therapeutically effective amount of at least one compound according to the following formula:

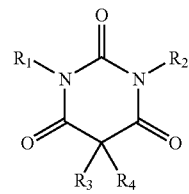

wherein $R_3$ and $R_4$ are each independently selected from the group consisting of lower alkyl, phenyl and lower alkyl substituted phenyl, and $R_1$ and $R_2$ are each independently either a hydrogen atom or a radical of the formula

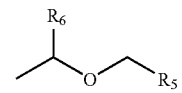

wherein $R_5$ and $R_6$ are each independently selected from the group consisting of H, lower alkyl, phenyl and lower alkyl substituted phenyl, its pharmaceutically acceptable salts, prodrugs or metabolites thereof.

22 Claims, 2 Drawing Sheets

U.S. PATENT DOCUMENTS

| | | | |
|---|---|---|---|
| 7,166,610 | B2 | 1/2007 | Moros |
| 7,214,658 | B2 | 5/2007 | Tobinick |
| 7,227,021 | B2 | 6/2007 | Gutman et al. |
| 7,683,071 | B2 | 3/2010 | Gutman et al. |
| 7,723,346 | B2 | 5/2010 | Moros et al. |
| 7,776,871 | B2 | 8/2010 | Moros |
| 2003/0018080 | A1 | 1/2003 | Gutman et al. |
| 2003/0153589 | A1 | 8/2003 | Moros et al. |
| 2003/0187005 | A1 | 10/2003 | Gutman et al. |
| 2004/0167358 | A1 | 8/2004 | Gutman et al. |
| 2004/0186120 | A1 | 9/2004 | Moros |
| 2004/0224947 | A1 | 11/2004 | Moros et al. |
| 2006/0004031 | A1 | 1/2006 | Gutman et al. |
| 2006/0009450 | A1 | 1/2006 | Tobinick |
| 2006/0035915 | A1 | 2/2006 | Gutman et al. |
| 2006/0122208 | A1 | 6/2006 | Gutman et al. |
| 2006/0205747 | A1 | 9/2006 | Moros et al. |
| 2006/0258864 | A1 | 11/2006 | Gutman et al. |
| 2007/0072886 | A1 | 3/2007 | Moros |
| 2007/0167624 | A1 | 7/2007 | Gutman et al. |
| 2008/0132529 | A1 | 6/2008 | Yacobi et al. |
| 2010/0144769 | A1 | 6/2010 | Gutman et al. |
| 2010/0311771 | A1 | 12/2010 | Moros |

FOREIGN PATENT DOCUMENTS

| | | |
|---|---|---|
| CN | 1461219 A | 12/2003 |
| DE | 946804 C | 8/1956 |
| DE | 1100639 B | 3/1961 |
| DE | 1103339 B | 3/1961 |
| DE | 1939787 A1 | 2/1970 |
| DE | 2622981 A1 | 12/1977 |
| DE | 4028040 A1 | 3/1992 |
| EP | 726252 A1 | 8/1996 |
| EP | 1083172 A1 | 3/2001 |
| GB | 966098 A | 8/1964 |
| JP | 60-084272 A | 5/1985 |
| JP | 08-104629 A | 4/1996 |
| JP | 2004-517808 A | 6/2004 |
| WO | WO-9918084 A1 | 4/1999 |
| WO | WO-0139779 A1 | 6/2001 |
| WO | WO-0179185 A1 | 10/2001 |
| WO | WO-0207729 | 1/2002 |
| WO | WO-03063872 | 8/2003 |
| WO | WO-03063872 A1 | 8/2003 |
| WO | WO-2004052350 A2 | 6/2004 |
| WO | WO-2006003651 A2 | 1/2006 |
| WO | WO-2006026095 A2 | 3/2006 |

OTHER PUBLICATIONS

Burgers Medicinal Chemistry and Drug Discovery, Fifth Edition, vol. I: Principles nad Practice, published 1994 by John Wiley & Sons, edited by Manfred E. Wolff, pp. 975-977.*
Stella, Valentino J, Expert Opinion of Therapeutic Patents, "Prodrugs as therapeutics," 2004 14(3): 277-280.*
Testa, Bernard, Biochemical Pharmacology, "Prodrug Research: futile or fertile?" vol. 68 (2004) pp. 2097-2106.*
Ettmayer, Peter, Medicinal Chemistry, Lessons Learned from Marketed and Investigational Prodrugs, vol. 47 No. 10 (2004) pp. 2394-2404.*
Pharmaceutical Chemistry, edited by Zhensu Li, published by Huaxue Gongye Chubaushe Publishers, 1981, p. 27.*
English translation of Pharmaceutical Chemistry, edited by Zhensu Li, published by Huaxue Gongye Chubaushe Publishers, 1981, p. 27.*
Gironell, A. et al., "A Randomized Placebo-Controlled Comparative Trial of Gabapentin and Propranolol in Essential Tremor", Archives of Neurology, Apr. 1999, vol. 56, No. 4: 475-480.
Doak et al., Pharmacotherapy, vol. 18, No. 3, pp. 637-645, 1998.
Glazco et al., Therapeutic Drug Monitoring, vol. 5, No. 4, pp. 409-417, 1983. (Abstract only).
Depakene Product Information, Abbott Laboratories, revised Apr. 2009.
Office Action Issued by the USPTO on Sep. 8, 2009, for U.S. Appl. No. 11/355,336.
Meriam Webster's Collegiate Dictionary, Tenth Edition, published 1998 by Merriam-Webster, Incorporated, pp. 924 and 935.
Office Action Issued by the USPTO on Dec. 28, 2009, for U.S. Appl. No. 10/865,428.
Ukkola et al., "Epilepsy After Operative Treatment of Ruptured Cerebral Aneurysms," Acta Neurochirurgica, vol. 106, pp. 115-118, 1990.
Office Action Issued by the USPTO on Jul. 8, 2009, for U.S. Appl. No. 10/856,428.
Office Action Issued by the USPTO on Jun. 30, 2009, for U.S. Appl. No. 11/201,024.
Office Action Issued by the USPTO on Sep. 28, 2007, for U.S. Appl. No. 11/355,339.
MedlinePlus Medical Encyclopedia, Convulsions, p. 1-4, last updated Jun. 26, 2008.
Office Action Issued by the USPTO on Jul. 16, 2008 for U.S. Appl. No. 11/355,336.
Office Action issued by the USPTO on Aug. 5 2008 for U.S. Appl. No. 10/865,428.
Office Action issued by the USPTO for U.S. Appl. No. 12/759,264 on Feb. 1, 2011.
Office Action issued by the U.S. Patent and Trademark Office for U.S. Appl. No. 12/689,757 on Jan. 6, 2011.
Ohannesian et al., eds. "Handbook of Pharmaceutical Analysis," Marcel Dekker, pp. 12-13, 2002.
Office Action issued by the USPTO for U.S. Appl. No. 12/759,264 on Jul. 14, 2011.
Aldrich Chemical Catalog, 1990-1991, p. 303.
Alexandre Gironell, et al., "A Randomized Placebo-Controlled Comparative Trial of Gabapentin and Propranolol in Essential Tremor" Archives of Neurology, Apr. 1999, vol. 56, No. 4: 475-480.
Alles et al. "Comparative central depressant actions of some 5-phenyl-5-alky barbituric acids" (J. Pharmacol Exp. Ther.) 1947, 89: 356-367.
Anthony E. Lang, et al. "Parkinson's Disease", Second of Two Parts, The New England Journal of Medicine, vol. 339, No. 16, Oct. 1998, pp. 1130-1143.
Appendix 1 of U.S. Appl. No. 60/352,273, filed Jan. 30, 2002: Chemical Derivative Chart (total of 8 pages).
Appendix 2 of U.S. Appl. No. 60/352,273, filed Jan. 30, 2002: References to Chemical Derivatives (total of 3 pages).
Appendix 3 of U.S. Appl. No. 60/352,273, filed Jan. 30, 2002: Cancerlit . . . (total of 9 pages).
Appendix 3 of U.S. Appl. No. 60/352,273, filed Jan. 30, 2002: MEDLINEplus printout of Jan. 15, 2002: Barbiturates (Systemic) (total of 14 pages).
Appendix 3 of U.S. Appl. No. 60/352,273, filed Jan. 30, 2002: PubMed search results printout of Jan. 15, 2002 (total of 7 pages).
Barnes, Harry M. et al., "For Further Observations on the Condensation of Benzene with Alloxan" (J. Am. Chem. Soc.) Jul.-Dec. 1937, 59: 2348-2351.
Bashir, K. et al.: "Clozapine for the control of hemiballismus," Clinical Neuropharmacology, vol. 17, No. 5, 1994, pp. 477-480, XP009032005.
Baumel et al. "Metabolism and anticonvulsant properties of primidone in the rat" (J. Pharmacol Exp. Ther.) 1973, 186: 305-314.
Beers et al., ed., Merck Manual of Diagnosis and Therapy, Seventeenth Edition, (1999), Chapter 179, pp. 1462-1473.
Berge et al. "Pharmaceutical Salts" Journal of Pharmaceutical Sciences (1977) vol. 66, No. 1, pp. 1-19.
Bertram et al., "Phenobarbital is superior to phenytoin as an antiepileptic, neuroprotectant and antiepileptogenic agent in a rat model of status epilepticus and chronic limbic epilepsy," Epilepsia, vol. 37, No. Suppl. 5, p. 140 (1996); and Annual Meeting of the American Epilepsy Society, San Francisco, CA, USA, Dec. 7-10, 1996.
Bhardwaj et al., "Pentobarbital inhibits extracellular release of dopamine in the ischemic striatum", Journal of Neural Transmission [Gen Sect], 82, pp. 111-117, (1990).
Boron Tribromide, Encyclopedia of Reagents for Organic Synthesis edited by Leo Pacquette, pp. 1-9, 2003.
Breimer et al. "Pharmacokinetics and relative bioavailbility of heptabarbital and heptabarbital sodium after oral administration to man" (Eur. J. Clin. Pharmacology) 1975, 9: 169-178.

Brint et al., "Focal brain ischemia in the rat: Methods for reproducible neocortical infarction using tandem occlusion of the distal middle cerebral and ipsilateral common carotid arteries", J. Cerebral Blood Flow Metab., 8, pp. 474-485, (1988).

Broderick et al., "Guidelines for the Management of Spontaneous Intracerebral Hemorrhage," Stroke, vol. 30, pp. 905-915, 1999.

Casagrande, C. et al., "Synthesis and antiarrhythmic activity of 5,5-disubstituted-3-aminoalkylhydantoins and some heterocyclic and noncyclic analogs", retrieved from STN Database accession No. 1975:43261, Farmaco, Edizione Scientific, 29(10) 757-785, 1974.

Casara et al., "Synthesis of acid stable fluorinated acyclonucleosides as potential antiviral agents," Tetrahedron Letters, 32(31) (1991), pp. 3823-3826.

Clinician, "Essential Tremor: A Practical Guide to Evaluation, Diagnosis, and Treatment" May 2001, vol. 19, No. 2, pp. 1-15.

Constantino et al., "Metabotropic glutamate receptors: targets for therapy of cerebral ischaemia," Expert Opinion on Therapeutic Drugs, vol. 5, pp. 669-683, 2001.

Corkill et al., Surg. Neurol., pp. 147-149 (1976).

Craig et al. "Metabolism and anticonvulsant properties of mephobarbital and phenobarbital in rats" (J. Pharmacol Exp. Ther.) 1971, 176: 35-41.

David E. Hartman, et al., "Spastic Dysphonia and Essential (Voice) Tremor Treated With Primidone", Arch Otolaryngol, vol. 110, Jun. 1984, pp. 394-397.

Dox et al "5,5-Diarylbarbituric Acids" (J. Chem. Soc.) 1923, 45: 1811-1816.

Elan D. Louis, "Essential Tremor", The New England Journal of Medicine, vol. 345, No. 12, Sep. 2001 pp. 887-891.

Enrico Sasso et al., "Primidone in the Long-Term Treatment of Essential Tremor: A Prospective Study with Computerized Quantitative Analysis", Clinical Neuropharmacology, vol. 13, No. 1, 1990, pp. 67-76.

Enrico Sasso, et al., "Double-Blind Comparison of Primidone and Phenobarbital in Essential Tremor"; Neurology, 1988, 38:808-810.

Enrico Sasso, et al., "Quantitative Comparison of Barbiturates in Essential Hand and Head Tremor", Movement Disorders, vol. 6, No. 1, 1991, pp. 65-68.

European Search report issued in EP Application EP 01 95 9195, dated Feb. 24, 2006.

European Search report issued in EP Application EP 05 29 0804, dated Jun. 16, 2005.

European Search report issued in EP Application No. 03 01 1817, completed Jul. 14, 2003.

European Search report issued in EP Application No. 03 73 5068, dated Feb. 28, 2006.

European Search report issued in EP Application No. 05 78 6192, dated Nov. 22, 2007.

Fink et al. "Modification of maximal audiogenic and electroshock seizures in mice by psychopharmacologic drugs" (J. Pharmacol Exp. Ther.) 1959, 127: 318-324.

Foye, "Principles of Medicinal Chemistry," 3rd ed. (1990) pp. 164, 179.

Gao et al., "Physical Chemical Stability of Warfarin Sodium,"AAPS Pharmasci (2001) 3(1) Article 3.

Garcia et al., "Neurological deficit and extent of neuronal necrosis attributable to middle cerebral artery occlusion in rats. Statistical validation", Stroke, 26(4), pp. 627-634, (1995).

Garcia et al., "Neuronal necrosis after middle cerebral artery occlusion in Wistar rats progresses at different time intervals in the caudoputamen and the cortex", Stroke, 26(4), 636-643 (1995).

Gesson et al., "A practical method for N-alkylation of succinimide and glutarimide", Bull Soc. Chim. Fr. 129, pp. 227-231, (1992).

Gibaldi et al. "Pharmokinetics Second Ed." 2nd Ed Marcel Dekker, Inc. 1982.

Ginsberg, "Animal Models of Global and Focal Cerebral Ischemia," Chapter 34 in Welsh KMA et al., Primer on Cerebrovascular Diseases, Academic Press, New York (1997).

Glazko et al. "Early adventures in drug metabolism: 2. The absorption of drugs" (Ther. Drug Monit.) 1987, 9: 180-89.

Glazko, A.J. "Diphenylhydatoin" (Pharmacology) 1972, 8: 163-177.

Goodman & Gilman's, The Pharmacological Basis of Therapeutics 2001, p. 412-419, 10th Ed.

Goodman & Gilman's, The Pharmacological Basis of Therapeutics, 9th Ed., 373-380 (1996).

Hamann, M. et al.: "Effects of striatal injections of GABAA receptor agonists and antagonists in a genetic animal model of paroxysmal dystonia," European Journal of Pharmacology, vol. 443, No. 1-3, May 17, 2002, pp. 59-70, XP002284223.

Hoff et al., Stroke, 6, pp. 28-33, (1975).

I. Balas et al. "Talamotomia esterotaxica de la enfermedad de Parkinson y otros tipos de temblor. Experiencias de la actividad multiunitaria burst en el talamo basada en semimicroelectrodos" Rev. Neurol., 2001, 32 (6): 520-524; I.. (English Abstract).

Iadarola et al. "Comparison of the effects of diphenylbarbituric acid, phenobarbital, pentobarbital and secobarbital . . . " (J. Pharmacol Exp. Ther.) 1985, 232: 127-133.

International Preliminary Examination Report issued in PCT Application No. PCT/US01/23420, completed on Feb. 23, 2003.

International Preliminary Examination Report issued in PCT Application No. PCT/US03/02638, completed on Oct. 31, 2003.

International Preliminary Examination Report issued in PCT Application No. PCT/US03/039530, completed on Mar. 10, 2005.

International Preliminary Report on Patentability issued in PCT Application No. PCT/IL2005/000697, issued on Jan. 9, 2007.

International Preliminary Report on Patentability issued in PCT Application No. PCT/US2005/028380, issued on Feb. 13, 2007.

International Search Report issued in PCT Application No. PCT/IL2005/000697, mailed on Oct. 13, 2006.

International Search Report Issued in PCT Application No. PCT/US01/23420, mailed on Nov. 20, 2001.

International Search Report Issued in PCT Application No. PCT/US03/02638, mailed on Jun. 18, 2003.

International Search Report issued in PCT Application No. PCt/US03/39530, mailed on Jul. 7, 2004.

International Search Report issued in PCT Application No. PCT/US04/041138, mailed on Aug. 10, 2005.

International Search Report issued in PCT Application No. PCT/US2005/028380, mailed on Dec. 8, 2006.

International Search Report issued in PCT Application No. PCT/US98/20665, mailed on Apr. 2, 1999.

IUPAC, Glossary of terms used in Medicinal Chemistry, pp. 1-10, 1998.

JAX ® Mice Literature, "Ask the Vet" No. 499 Published online in fall 2005 at http://jaxmice.jax.org/library/notes/499c.html.

Kamata et al., "Studies of Antitumor-Active 5-Fluorouracil Derivatives I Synthesis of N-Phthalidyl 5-Fluorouracil Derivatives", Chem. Pharm. Bull, 33 (8), pp. 3160-3175, (1985).

Karger et al., "Methoxymethyl Methanesulfonate, A Novel Active Oxyalkylating Agent," J. Am. Chem. Soc., 91:5663 (1969)

Knoefel et al. "The anticonvulsant action of diphenylhydatoin and some related compounds" (J. Pharmacol Exp. Ther.) 1942, 76: 194-201.

Kojima et al., J. Pharm Sci. 60: 1639-1641 (1971).

Kojima, Chem. Pharm. Bull. 21 (11): 2432-2437 (1973).

L.J. Findley et. al., C.D. Marsden, Origins of Normal and Pathological Tremor in Movement Disorders: Tremor. Eds., New York, Oxford University Press, 1984, pp. 37-84 "Origins of Normal and Pathological Tremor".

Leslie J. Findley et al., "Primidone in Essential Tremor of the Hands and Head: A Double Blind Controlled Clinical Study", Journal of Neurology, Neurosurgery, and Psychiatry, 1985: 48, No. 9, 911-915.

Leslie J. Findley, "Epidemiology and Genetics of Essential Tremor", Neurology, Jun. 2000, vol. 54, Suppl 4, S8-S13.

Leslie J. Findley, "The Pharmacology of Essential Tremor", Movement Disorders 2, 1987, (22) 438-458.

Leslie J. Findley, et al., "Primidone in Essential Tremor of the Hands and Head: A Double Blind Controlled Clinical Study" Journal of Neurology, Neurosurgery, and Psychiatry 1985;48:911-915.

Leslie J. Findley, et al., "Phenobarbitone in Essential Tremor", Neurology, 1985, 35:1784-1787.

Levy et al., "Delayed pentobarbital administration limits ischemia brain damage in gerbils", Annals of Neurology, 5(1), pp. 59-64, (1979).

Lightfoote, et al., Stroke, 8, pp. 627-628, (1977).

Loudon, "Organic Chemistry", Addison-Wesley (1984), pp. 617, 721-722, 1061-1064, 1086-1088, 1194.

Malhotra, S. et al., "T-2000, a novel non-sedating barbiturate reduces infact size and improves neurologic functions following MCAO in the rat," Program No. 821.10. 2004 Abstract Viewer/Itinerary Planner. Washington, DC: Society for Neuroscience, 2004. Online.

Manfred D. Muenter, et al. "Treatment of Essential Tremor With Methazolamide" Mayo Clinic Proceedings, vol. 66, No. 10, Oct. 1991, pp. 991-997.

Masuda et al., "Relationships Between Plasma Concentrations of Diphenylhydantoin, Phenobarbital, Carbamazepine, and 3-Sulfamoylmethyl-1,2-Benzisoxazole (AD-810), a New Anticonvulsant Agent, and Their Anticonvulsant or Neurotoxic Effects in Experimental Animals", Epilepsia, 20, pp. 623-633, (1979).

McElvain, "5.5-diphenylbarbituric acid" J. Am. Chem. Soc. (1935) vol. 57, pp. 1303-1304.

McKeown et al. "Thermodynamic functions for dissociation of 5,5-disubstituted barbituric acids- their signficance in structure-reactivity . . . " (Ellis Horwood) 1986, 6: 80-89.

Merritt et al. "Experimental determination of anticonvulsive activity of chemical compounds" (Epilepsia) 1945, 3: 51-75.

Nims et al. "Compartive pharmacodynamics of hepatic cytochrome $P4_{50\,2B}$ induction by 5,5-diphenyl- and 5,5-diethyl substituted . . . " (J. Pharmacol. Exp. Ther.) 1994, 270: 348-355.

Office Action Issued by the USPTO on Apr. 20, 2009, for U.S. Appl. No. 11/201,024.

Office Action issued by the USPTO on Apr. 22, 2009 for U.S. Appl. No. 10/865,428.

Office Action issued by the USPTO on Dec. 5, 2007 for U.S. Appl. No. 11/201,024.

Office Action Issued by the USPTO on Feb 25, 2009, for U.S. Appl. No. 11/355,336.

Office Action issued by the USPTO on Jan. 11, 2008 for U.S. Appl. No. 11/727,557.

Office Action Issued by the USPTO on Mar. 24, 2009, for U.S. Appl. No. 11/169,044.

Office Action Issued by the USPTO on Mar. 6, 2009, for U.S. Appl. No. 11/355,339.

Office Action issued by the USPTO on Nov. 1, 2007 for U.S. Appl. No. 10/865,428.

Office Action issued by the USPTO on Oct. 5, 2007 for U.S. Appl. No. 11/355,336.

Ondo, W. et al.: "Essential tremor. Treatment Options," CNS Drugs 1996 New Zealand, vol. 6, No. 3, 1996, pp. 178-191, XP009032012.

P. Dietrichson, et al., "Primidone and Propranolol in Essential Tremor: A Study Based on Quantitative Tremor Recording and Plasma Anticonvulsant Levels", Acta Neurol Scand., 1987:75:332-340.

Paul G. Wasielewski, et al. "Pharmacologic Treatment of Tremor", Movement Disorders, vol. 13, Suppl 3., pp. 90-100, 1998.

Piatt, et al., "High dose barbiturate therapy in neurosurgery and intensive care," Neurosurgery, vol. 15, No. 3, Sep. 1984, pp. 427-444.

Prankerd et al. "Physio-chemical properties of barbituric acid derivatives: IV. Solubilities of 5,5-disubstituted barbituric acids . . . " (Int. J. Pharmaceutics) 1994, 112: 1-15.

PubMed search results printout of Dec. 27, 2002 (total of 3 pages).

Pulsinelli et al., "A new model of bilateral hemispheric ischemia in the unanesthetized rat", Stroke, May-Jun. 10(3), pp. 267-272, (1979).

Pulsinelli et al., "Temporal profile of neuronal damage in a model of transient forebrain ischemia", Annals of Neurology, May 11(5), 491-498, (1982).

Raines et al. "Pre and postjunctional effects of diphenylhydantoin at the cat soleus neuromuscular junction" (J. Pharmacol Exp. Ther.) 1966, 153: 361-366.

Raines et al., "A Comparison of the Anticonvulsant, Neurotoxic and Lethal Effects of Diphenylbarbituric Acid Phenobarbital and Diphenylhydantoin in the Mouse," J. Pharmacology and Experimental Therapeutics, 186(2):315-322 (1973).

Raines et al., "Anticonvulsant properties of 5,5-diphenylbarbituric acid (DPB)" (Pharmacology) 1973, 32: 3246.

Raines et al., "Conversion of Dimethoxymethyl-Diphenylbarbituric Acid (DMMDPB) to Diphenylbarbituric Acid (DPB) in the Dog," The FASEB J., 13(4):A475, Abstract 394.2 (1999).

Raines et al., "Conversion of Dimethoxymethyl-Diphenylbarbituric Acid (DMMDPB) to Diphenylbarbituric Acid (DPB) in the rat," The FASB J., 1996, Abstract No. 895.

Raines et al., "Differential selectivity of Severla Barbiturates on Experimental Seizures and Neurotoxicity in the Mouse" Epilepsia (1979) vol. 20, pp. 105-113.

Raines et al., "The Effects of 5,5-Diphenylbarbituric Acid on Experimental Seizures in Rats: Correlation between Plasma and Brain Concentrations and Anticonvulsant Activity," Epilepsia, 16:575-581 (1975).

Raines et al., Chemical Abstracts, 79:87539k, 1973.

Raines et al., Chemical Abstracts, 92:174402x, 1980.

Raines, et al.,"Serum and Brain Levels of 5-5-Diphenylbarbituric Acid (DPB) After Administration of dimethoxymethyl-Diphenylbarbituric Acid (DMMDPB) in the Rat," Epilepsia, 37:Supp. 5, p. 23, Abstract 1.84 (1996).

Rekling Jens C., "Neuroprotective effects of anticonvulsants in rat hippocampal slice cultures exposed to oxygen/glucose deprivation", Neuroscience Letters, vol. 335, No. 3, Jan. 2, 2003, pp. 167-170.

Remington: The Science and Practice of Pharmacy, 20th Edition; Published 2000 by Lippincott Williams and Wilkins, Edited by Daniel Limmer, pp. 317-322.

Remington: The Science and Practce of Pharmacy 20th edition, published 2000 by Lippincott Williams and Wilkins, pp. 704-714, 743-747 and 858-863.

Ropper et al., "Adams and Victor's Principles of Neurology" (8th ed., 2005), pp. 338-339, 895-958.

Salmon-Legagneur et al., "Recherches dans la serie des diacides .alpha..alpha.-disubstitues et de leurs derives. III. Les acides .alpha.-phenol .alpha.-alcoyl (ou phenoalcoyl) glutariques et leurs principaux derives", Bull. Soc. Chim. France (1953) p. 70.

Salmon-Legagneur et al., "Sur les acides .alpha.-pheyl .alpha.-alcoyl (ou phenoalcoyl) glutariques", Comptes Rendus de l'Academie des Sciences, (Mar. 3, 1952) p. 1060.

Samour et al., "Anticonvulsants, 1. Alkoxymethyl Derivatives of Barbiturates and Diphenylhydantoin", Journal of Medicinal Chemistry, 14 (3), pp. 187-189, (1971).

Sasso, E. et al.: "Double-Blind Comparison of Primidone and Phenobarbital in Essential Tremor," Neurology, vol. 38, No. 5, 1988, pp. 808-810, XP009032012.

Selleri, R. et al., "N1, N3-Disubstituted barbituric acid derviates of ganglioplegic or curarelike action", retrieved from STN Database accession No. 1959:111820, Farmaco, Edizione Scientifica, 12, 3-14, 1957.

Serrano et al. "Intramuscular administration of diphenylhydantoin" Arch. Neurol., Oct. 1974, 31: 276-277.

Shapiro, "Barbiturates in Brain Ischaemia," British Journal of Anaesthesia, BJM Publishing Group, London, Great Britain, vol. 57, No. 1, Jan. 1985, pp. 82-95.

Sircar, "CLXXIII.—The Influence of Groups and Associated Rings on the Stability of Certain Heterocyclic Systems. Part II. The Substituted Succinimides"; Journal of the Chemical Society, May 1927, pp. 1252-1258.

Stanley Fahn, et al. "Clinical Rating Scale for Tremor", Parkinson's Disease and Movement Disorders, Urban & Schwarzenberg, Inc., 1988, 17: 225-234.

Stavber et al., Chemical Abstracts, 99:157381s, 1983.

Sturfelt, G. et al.: Acute Effects of Barbiturates in Parkinson's Disease, "Acta Medica Scandinavica, Almqvist & Wiksell Periodical Co.;" Stockholm, SE, vo. 201, No. 1/2, 1977, pp. 75-76, XP000937405.

Swanson et al., "Barbiturates impair astrocyte glutamate uptake," GLIA, Dec. 1998, vol. 34, No. 4, Dec. 1998, pp. 365-371.

Tagmann et al., Helv. Chim. Acta 35, 1541-1549 (1952).

Thacker et al., "Method for the Determination of 5,5-Diphenylbarbituric Acid and Separation from 1,3-Dimethoxymethy1-5,5-Diphenylbarbituric Acid in Plasma by High Performance Liquid Chromatography," J. Chromatography B. 710:149-155 (1998).

The Merck Index, 10th Ed., (Merck & Co., Inc., Rahway, NJ) (1983) p. 544 (entry 3694).

Theodore E. Gram "Metabolism of Drugs", Modern Pharmacology, 2nd Ed., 1986, Ch. 4, pp. 41-64.

Vida et al., "Anticonvulsants. IV. Metharbital and phenobarbital derivatives" Journal of Medicinal Chemistry, vol. 16, No. 12, pp. 1378-1381, 1973.

Vida J. A. et al, "Anticonvulsants. III. Phenobarbital and mephobarbital derivatives", Journal of Medicinal Chemistry 1973, vol. 16, p. 602-605.

Vida J. A. et al, "Anticonvulsants. IV. Metharbital and phenobarbital derivatives" Journal of Medicinal 1378-1381, (1973) vol. 16 No. 12.

Vida J. et al., "Anticonvulsants. 2. Acyloxymethyl and halomehtyl derivaitives of barbituric acid and diphenylhydantoin", Journal of Medicinal Chemistry, 14(3): p. 190-193, Mar. 1971.

W.P. Gorman, et al., "A Comparison of Primidone, Propranolol, and Placebo in Essential Tremor, Using Quantitative Analysis", Journal of Neurology, Neurosurgery, and Psychiatry 1986;49:64-68.

Weinryb et al., Chemical Abstracts, 76:1206c, 1972.

Werner W. et al., "Structure effect interactions in Mannich bases with and without nitrogen mustard groups and some reference compounds as potential immunosuppressive agents", retrieved from STN Database accession No. 85: 72035, Pharmazie 31(5) 282-7, 1976.

Whittle et al. "Differential effect of sedative and anticonvulsant barbiturates on specific gaba binding to membrane prep . . . " (Bio. Pharmacology) 1982, 31: 2891-2895.

Wiley Miller, ed., "Stroke Therapy: Basic, preclinical, and clinical directions", (1999).

William C. Koller et al., "Pharmacologic Treatment of Essential Tremor", Neurology, Jun. 2000 vol. 54, Supp.l 4, S30-S38.

William C. Koller, et al. Long Term Safety and Efficacy of Unilateral Deep Brain Stimulation of the Thalamus in Essential Tremor, Movement Disorders, vol. 16, No. 3, 2001 pp. 464-468.

William C. Koller, et al., "Essential Tremor Variants: Effect of Treatment", Clinical Neuropharmacology vol. 10, No. 4, 1987, pp. 342-350.

William C. Koller, et al., "Efficacy of Primidone In Essential Tremor", Neurology, 1986; 36:121-124.

William R. Hobbs et al., "Hypnotics and Sedatives; Ethanol". Goodman & Gilman's The Pharmacological Basis of Therapeutics, 9th Ed. Ch. 17, 361-396, (1996).

Written Opinion issued in PCT Application No. PCT/US04/041138, mailed on Aug. 10, 2005.

Xiao-Ming Guan et al., "Basic Mechanism of Action of Drugs Used in the Treatment of Essential Tremor", Clinical Neuropharmacology, vol. 13, No. 3, 1990, pp. 210-223.

Yeh et al. "A comparison of numerical integrating algortihms by trapezoidal, lagrange, and spline approximations." (J. Pharmacokinet Biopharm) 1978, 6: 79.

Zavadil et al., Effects of Diphenylbarbituric Acid on Neuromuscular and Spinal Cord Function in the Cat, Neuroscience Abstracts, p. 694 (1975).

Zavadil III, et al. "Diphenylbarbituric Acid" (Epilepsia) 1985, 26: 158-166.

* cited by examiner

METHOD OF TREATING MOVEMENT DISORDERS USING BARBITURIC ACID DERIVATIVES

This application is a continuation of U.S. patent application Ser. No. 11/355,339 filed Feb. 16, 2006, which is a continuation of U.S. patent application Ser. No. 10/735,514 filed Dec. 11, 2003, now U.S. Pat. No. 7,166,610, which claims the benefit of U.S. Provisional Application Ser. No. 60/432,470, filed Dec. 11, 2002, the entire contents of which are incorporated herein by reference.

FIELD OF THE INVENTION

The present invention relates to the treatment of movement disorders, such as essential tremor, through the administration of one or more of 5,5 diphenyl barbituric acid and derivatives thereof.

BACKGROUND OF THE INVENTION

Movement Disorders

Movement disorders include a wide variety of disease states and physiological conditions. Non-limiting examples include various dyskinesias such as tremor, dystonia, chorea, athetosis, tic disorders, blepharospasm, as well as hemiballysmus, myoclonus, focal dystonias, such as writer's cramp and torticollis, restless leg syndrome and asterixis. These excessive or otherwise abnormal involuntary movements may vary significantly in rate, frequency, periodicity and progressionary character. Such movements may be seen in sometimes overlapping disorders such as Parkinson's disease; essential tremor, a.k.a. benign tremor or familial tremor; tic disorders, e.g. Tourette's syndrome; idiopathic dystonia (inducing writer's cramp), progressive supranuclear palsy and Wilson's disease. Movement disorders are different from seizure disorders in that movement disorders are often suppressible, they often subside or are absent during sleep and are distractable and not associated with the loss of consciousness.

Tremor is the most common of all movement disorders. Tremor is defined as an involuntary rhythmic, oscillatory movement about a joint produced by contractions of reciprocally innervated agonist/antagonist muscles, and is repetitive and regular in frequency. (Essential Tremor: *A Practical Guide to Evaluation, Diagnosis, and Treatment, Clinician*, Vol. 19 (No. 2), pgs. 1-15, 2001). It also ranks as one of the most debilitating symptoms in all of neurology. For example, the presence of even mild tremor in the upper extremities can make even the simplest of tasks impossible to perform. (Wasielewski P. G. et al., Pharmacologic Treatment of Tremor, *Movement Disorders*, Vol. 13, Supplement 3, 1998, pp 90-100). Essential tremor and tremor associated with Parkinson's disease are the most common types of tremor encountered in clinical practice. (Wasielewski P. G. et al., Pharmacologic Treatment of Tremor, *Movement Disorders*, Vol. 13, Supplement 3, 1998, pp 90-100).

Essential tremor is the most common form of tremor and of all movement disorders and perhaps the most common primary neurological disorder. Estimates of the prevalence in the elderly population range from 1 to 22%, with 1-2% being a conservative number. (Findley L. J., Epidemiology and Genetics of Essential Tremor, *Neurology,* 2000, 54 (Suppl. 4), S8-S13). While often a minor problem and unassociated with other disease (hence the term "benign tremor or benign essential tremor"), it causes significant motor impairment for many individuals. In its classic form, it is a tremor involving the upper extremities and/or the head. Usually, it has a frequency of 5-8 Hz, is absent with rest, presents with a sustained posture and is not significantly exacerbated by movement. (Marsden C D. Origins of Normal and Pathological Tremor in Movement Disorders: *Tremor*. Eds. L. J. Findley and R. Capildeo, New York. Oxford University Press, 1984, pp. 37-84).

The cause and pathophysiology of essential tremor remain unknown. No pathologic substrate has been demonstrated in autopsy studies. Positron emission tomography (PET) studies of glucose metabolism and blood flow have demonstrated only general findings of increased activity in the brain stem (medulla), thalamus, cerebellum, striatum and sensorimotor cortex.

Parkinson's disease is a progressive disorder with a prevalence of 1-2% in people over the age of 50. It has a worldwide distribution and has no gender preference. Unlike essential tremor, untreated Parkinson's disease is life shortening. Symptoms of the disease include (1) shaking of the hands, arms, legs or feet while the patient is resting (the shaking may be more noticeable on one side of the body, and it may affect the hands more than the feet, the shaking often stops, however, as soon as the patient moves his limbs); (2) slowness of movement or a brief, temporary delay in movement; (3) difficulty in maintaining one's balance; (4) rigidity or stiffness of the patient's limbs; (5) facial masking (a still facial expression with fewer blinks of the eyes); (6) difficulty in speech; (7) difficulty swallowing; and (8) chorea and dystonic posturing, particularly as a side effect of treatment with dopaminergic agents. As the Parkinson's disease progresses, patients may be forced to work fewer hours and cut back on their activity level. Simple tasks become more of a challenge, and they may need some help from family and friends. Patients may find that using a wheelchair helps them move around more easily, and they may need help with daily activities.

Current Treatment of Movement Disorders

1. Treatment of Essential Tremor

Alcohol remains the most effective single agent for treatment of essential tremor. Estimates of patients responsive to alcohol range from 50-90%. (Koller, W. C., Hristove, A., Brin, M. Pharmacologic Treatment of Essential Tremor. Neurology 2000; 54 (Suppl 4), pp. S30-S38.) Its effect may be dramatic in some individuals. However, the half-life of alcohol is brief and the side effects are numerous.

Beta-adrenergic receptor blocking agents such as propranolol have also been widely used for over 30 years. However, even when beneficial, the clinical response is variable and incomplete. Moreover, beta-adrenergic blockers are probably of no benefit in 50% or more of patients.

The anticonvulsant primidone has been demonstrated to be effective in a significant subpopulation of patients. Comparative studies of primidone and beta-blocking agents variously report either therapeutic equivalency or slightly greater efficacy for primidone. Primidone, unlike beta-blocking drugs, will completely suppress tremor in some patients. (Findley, L. J., Cleeves, L., Caletti, S. Primidone in Essential Tremor of the Hands and Head: A Double Blind Controlled Clinical Study. *J. Neurol Neurosurg Psych,* 1985, 48, pp. 911-915.) Primidone, however, produces a high incidence of side effects. Furthermore, primidone has little or no effect on head tremor, even in patients with a positive response of the limbs. Primidone is converted into two active metabolites, phenobarbital and phenylethylmalonamide (PEMA). PEMA has been found to have no anti-tremor effect.

Phenobarbital has some anti-tremor effect, but not as prominent as primidone or beta-blocking agents, particularly when the patients are assessed in terms of functional improvement. (Findley, L. J. The Pharmacology of Essential Tremor in *Movement Disorders* 2$^{nd}$ Edition. Morsden, C. D., Fahn S, Longdong: Butterworths, 1987. As detailed below, phenobarbital has sedative effects and can suppress respiration.

There have been brief reports of newer anticonvulsant drugs, particularly gabapentin, providing a benefit in treatment of essential tremor. (See Gironell, A., Kulisevsky, J., Lopez-Villegas, D., Hernandez, G., Pascual-Sedano, B., A Randomized Placebo-Controlled Comparative Trial of Gabapentin and Propanolol in Essential Tremor. *Arch. Neurol.*, 1999, 56, pp. 475-480.) None of these other agents, however, have gained wide use for this indication, presumably because of their neurological side effects and/or limited efficacy. Methazolamide, a carbonic anhydrase inhibitor, has been reported to be of some benefit. (Meunter, M. D., Daube, J. R., Caviness, J. N., Miller, P. M. Treatment of Essential Tremor with Methazolamide. *Mayo Clinic Proc*, 1991, 66, pp. 991-997.) However, primidone and propranolol are the only two prescription drugs with proven efficacy in general clinical practice. Louis, E. D., *N Eng. J. Med.*, 345, (12), 2001, pp. 887-891.

U.S. Pat. No. 6,281,207 to Richter et al. discloses methods of combating movement disorders such as tremor by administering mirtazapine.

Surgical treatment of severe disabling essential tremor is sometimes useful. This has most commonly involved thalamotomy (lesioning of the thalamus) and, more recently, the use of surgically implanted electrodes. These procedures however have considerable potential morbidity.

Therefore, there exists a need for a method of treating essential tremor and other movement disorders having minimal adverse side effects, high tolerance, and significant effectiveness.

2. Treatment of Parkinson's Disease

The most widely recognized drug for the treatment of Parkinson's disease is levodopa, a medication that is converted into dopamine when it crosses into the brain. Levodopa reduces the symptoms of this disease because dopamine is the chemical that is necessary for human muscles to function normally. It is called a replacement drug because it replaces dopamine. For most patients with Parkinson's disease, levodopa provides significant improvement in many symptoms, including tremor. However, the therapeutic benefits of this drug usually last for only a limited period of time. After about 3 to 5 years of treatment, levodopa becomes less effective in reducing symptoms in most patients. At times the patient can move around easily or with slight tremor and rigidity, and at other times the patient has difficulty with movement, as if the medicine is "wearing off" For this reason, doctors try to keep the dose of levodopa as low as possible or may not begin treatment with levodopa until the symptoms can no longer be managed by other means. (Lang, A. E. et al., *N. Eng. J. Med*, 339 (16), 1998, pp. 1130-1143).

The side effects of levodopa include nausea, vomiting, loss of appetite, rapid heart rate, and lowered blood pressure when a person stands from a sitting position. To reduce these side effects, levodopa is often prescribed in combination with carbidopa, and this drug combination is marketed under the trademark Sinemet™ (Bristol-Myers Squibb). The carbidopa in Sinemet™ prevents levodopa from being metabolized in the stomach and liver, so more of the levodopa can get to the brain, which permits administration of a smaller dose of levodopa or alternatively increases the effectiveness of a given administered dose of levodopa. Even though carbidopa helps to reduce the side effects of levodopa, many patients who take Sinemet™ may still experience nausea, vomiting, and loss of appetite when they begin taking it or after their dosage is increased. Other side effects of carbidopa/levodopa combination medications include dry mouth, daytime sleepiness, nervousness, vivid dreams, insomnia, and a form of motor fluctuation called dyskinesia, characterized by involuntary writhing movements. Sometimes dyskinesia results when the dosage of the medication is too high.

Another group of medications for Parkinson's Disease is dopamine agonists. Dopamine agonists are drugs that stimulate the parts of the human brain that normally respond to dopamine. In effect, the brain "thinks" it is receiving dopamine, so these drugs help satisfy the brain's need for dopamine. The most commonly used dopamine agonists in the United States include Parlodel™ (bromocriptine, Novartis), Permaxrm (pergolide mesylate, Amarin), MIRAPEX™ (pramipexole hydrochloride, Pharmacia & Upjohn) and Requip™ (ropinirole, GlaxoSmithKline). Parlodel™ and Permax™ are synthetic derivatives of a chemical called "ergot". The side effects are similar to those of levodopa: nausea, vomiting, confusion, hallucinations, lightheadedness and fainting. A rare side effect known as fibrosis (membrane lining of body organs can become thickened or scarred) has also been reported. MIRAPEX™ has been shown to be effective in treating the symptoms of early disease without levodopa. During the advanced stages, taking MIRAPEX™ in combination with levodopa may reduce the dose of levodopa that is needed. The use of MIRAPEX™ can cause drowsiness and the possibility of suddenly falling asleep during daily activities, which could result in an accident while driving. The most common side effects of MIRAPEX™ are nausea, sleeplessness, constipation, involuntary movement, sleepiness, dizziness upon standing, and hallucinations.

Another group of medications for Parkinson's Disease is catechol-O-methyltransferase (COMT) inhibitors (e.g., Tasmar™ (tolcapone, Roche Laboratories) and Comtan™ (entacapone, Novartis)). COMT is one of two enzymes that break down levodopa before the brain converts it into dopamine. When the COMT enzyme is blocked by the COMT inhibitors, dopamine stays in the brain for a longer period of time. COMT inhibitors are usually taken with levodopa. The most common side effects reported by patients who have taken COMT inhibitors include unusually vivid dreams or visual hallucinations, nausea, difficulty in sleeping, daytime drowsiness, headache, and excessive involuntary movements. In addition, in 1998 the U.S. Food and Drug Administration reported that Tasmar™ can cause liver damage, so now doctors are advised to monitor their patients who are taking this drug on a regular basis to make sure their liver is functioning normally.

Anticholinergics have also been used in the treatment of Parkinson's disease. Before doctors begin treating Parkinson's disease patients with levodopa, they may prescribe anticholinergic drugs such as Artane™ to relieve symptoms. When the brain cannot get enough dopamine, it produces increased quantities of a chemical called acetylcholine, and too much acetylcholine causes tremor and rigidity in patients. Anticholinergic drugs block the effect of acetylcholine, so they are effective in reducing tremor and rigidity in patients. Anticholinergics are not usually prescribed for long periods of time because of the side effects they cause in patients, which include dry mouth, blurred vision, constipation, difficulty in urinating, confusion, and hallucinations.

Dopamine is broken down in the brain by an enzyme called monoamine oxidase (MAO). Hence, selegiline and other MAO inhibitors help the brain make the most of the dopamine that is still being produced and/or dopamine that is being supplied to the brain by other drugs. When a Parkinson's disease patient takes an MAO inhibitor, it slows down the progress of this enzyme, which increases the amount of dopamine that is available to the brain. The side effects of selegiline include heartburn, loss of appetite, nausea, dry mouth, dizziness, constipation, and insomnia.

Anti-viral agents such as Symmetrel™ (amantadine, Endo Labs) provide mild relief of Parkinson's symptoms in newly-diagnosed patients. It has been used to treat this disease for many years, but even today, medical researchers and doctors aren't really sure how it works in the human brain. Unfortunately, it tends to cause insomnia and daytime fatigue, and other side effects that have been reported include red or purple skin blotches (often on the patient's legs), swelling of the feet, anxiety, dizziness, difficulty in urinating, and hallucinations. (Lang, A. E. et al., *N Eng. J. Med.,* 339 (16), 1998, pp. 1130-1143).

U.S. Pat. No. 6,281,207 to Richter et al. discloses methods of combating movement disorder such as Parkinson's disease by administering mirtazapine.

Surgery can dramatically reduce symptoms for some patients in the advanced stages of Parkinson's disease. Doctors may suggest surgery as an option for such patients because they have been taking combinations of drugs over a long period of time, and those drugs have become less and less effective. A pallidectomy or pallidotomy is a surgical procedure in which a lesion is created in a specific area of the brain (globus pallidus) to help restore the balance required for normal motion. The majority of patients who have had this surgery have gained immediate, significant improvements in their ability to function, and those benefits have lasted for at least a year. Deep brain stimulation (DBS) has also been used by physicians as a preferred alternative to a pallidotomy. Although these surgical approaches have produced some desirable results, the long-term effects of such surgeries for Parkinson's patients are not yet known. Therefore, doctors generally reserve these as last resort treatments for their patients. (Lang, A. E. et al., *N. Eng. J. Med,* 339 (16), 1998, pp. 1130-1143).

In view of the above, there exists a need for a method of treating movement disorders that are either symptoms of or associated with Parkinson's disease or not using an active agent having minimal adverse side effects, high tolerance, and significant effectiveness.

Barbituric Acid Derivatives

1. Sedating Barbituric Acid Derivatives

Barbiturates (or barbituric acid derivatives) have been developed and have been used as the primary drugs for the treatment of insomnia for many years. Barbiturates depress both the respiratory drive and the mechanisms responsible for the rhythmic character of respiration. (Goodman & Gilman's, *The Pharmacological Basis of Therapeutics*, Chapter 17, 9$^{th}$ Edition, McGraw-Hill). They have been implicated in thousands of deaths due to accidental (or deliberate) ingestion (resulting in homicide, suicide or accidental death) since they are associated with serious, often fatal, central nervous system (CNS) depressive effects following acute overdosage. Barbiturates have been chronically abused by a substantial portion of the population. When coadministered with other drugs, barbituatates may interact with them with a potentially lethal outcome. Currently or previously clinically employed barbiturates include amobarbital, barbital, butabarbital, and hexobarbital, mephobarbital, pentobarbital, phenobarbital, secobarbital, thiamylal, and thiopental. Barbiturates with a short to intermediate duration of action (e.g., amobarbital, butabarbital, pentobarbital, secobarbital, and vibarbital) are used as sedative-hypnotics. Phenobarbital is used as an anti-convulsant for the treatment of seizure disorders. Ultrashort-acting barbiturates (e.g., thiamylal and thiopental) can be used as anesthetics. (Craig, C. R. and Stitzel R. E., Modern Pharmacology, Chapter IV, 2nd Edition, 1986, Little, Brown and Company, Boston/Toronto).

As mentioned above, sedative barbiturates such as phenobarbital have been found to have some anti-tremor effect. However, its effectiveness is severely limited by its strong side effects.

2. Non-Sedating Barbituric Acid Derivatives

U.S. Pat. No. 4,628,056 ("the '056 Patent") to Levitt et al. discloses novel oxopyrimidine derivatives of the general formula

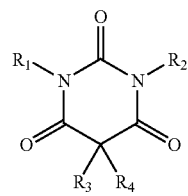

wherein $R_1$ and $R_2$ may be the same or different and are each hydrogen or lower alkyl optionally substituted by lower alkoxy, and $R_3$ and $R_4$ may be the same or different and are each phenyl optionally substituted by lower alkyl or halogen, provided that when $R_1$ and $R_2$ are both hydrogen, $R_3$ and $R_4$ are each substituted phenyl. The '056 Patent discloses that these compounds are useful as anticonvulsants, and antianxiety agents and as muscle relaxants. According to the '056 Patent, animals given such compounds continue to behave normally and do not show any observable effects on locomotion, escape behavior or feeding behavior. The '056 Patent further elaborates that the compounds disclosed therein are useful in treating mammals for strain and stress conditions and nervous dysfunctions such as convulsions, seizure, muscle stiffness, nervous strain and anxiety. The '056 Patent does not mention or suggest that such compounds can be used to treat any movement disorders.

U.S. Pat. No. 6,093,820 ("the '820 Patent") to Gutman et al. discloses that alkoxyalkylated ureide compounds such as N-methoxymethyl ethosuximide, N-methoxymethyl glutethimide, and N-methoxymethyl-5,5-diphenylbarbituric acid are also useful in treating convulsions, seizures, muscle stiffness, or anxiety. Again, the '820 Patent doses not mention or suggest that any of these compounds can be used to treat any movement disorders.

SUMMARY OF THE INVENTION

The present invention provides a method of treating movement disorders comprising administering an amount effective for that purpose of at least one compound according to the following formula (1):

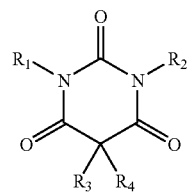

wherein $R_3$ and $R_4$ are each independently selected from the group consisting of lower alkyl, phenyl and lower alkyl substituted phenyl, and R₁ and R₂ are each independently either a hydrogen atom or a radical of the formula

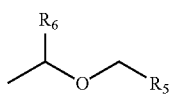

wherein R₅ and R₆ are each independently selected from the group consisting of H, lower alkyl, phenyl and lower alkyl substituted phenyl; or a pharmaceutically acceptable salt, prodrug or metabolite thereof.

In one embodiment, the movement disorder treated with one or more of the foregoing compounds is essential tremor.

In another embodiment, the movement disorder is tremor and/or dystonia or chorea associated with Parkinson's disease.

In yet another embodiment, the movement disorder is not associated with Parkinson's disease.

In a further embodiment, the movement disorder is a focal dsytonia, such as writer's cramp.

In yet a further embodiment, the movement disorder is restless leg syndrome.

According to a preferred embodiment of the present invention, a method of treating essential tremor comprises administering an amount effective for that purpose of at least one compound according to the following formula (II):

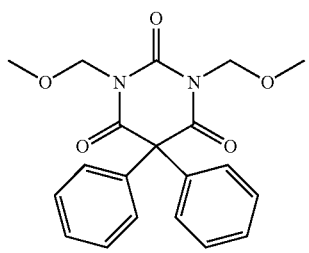

or a pharmaceutically acceptable salt, prodrug or metabolite thereof.

According to another preferred embodiment of the present invention, a method of treating essential tremor comprises administering an amount effective for that purpose of at least one compound according to the following formula (III):

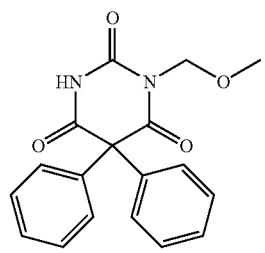

or a pharmaceutically acceptable salt, prodrug or metabolite thereof.

According to a further preferred embodiment of the present invention, a method of treating essential tremor comprises administering an amount effective for that purpose of at least one compound according to the following formula (IV):

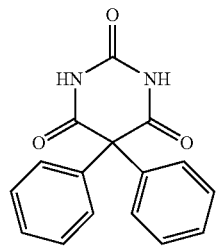

or a pharmaceutically acceptable salt, prodrug or metabolite thereof.

DETAILED DESCRIPTION OF THE INVENTION

Figure 1:
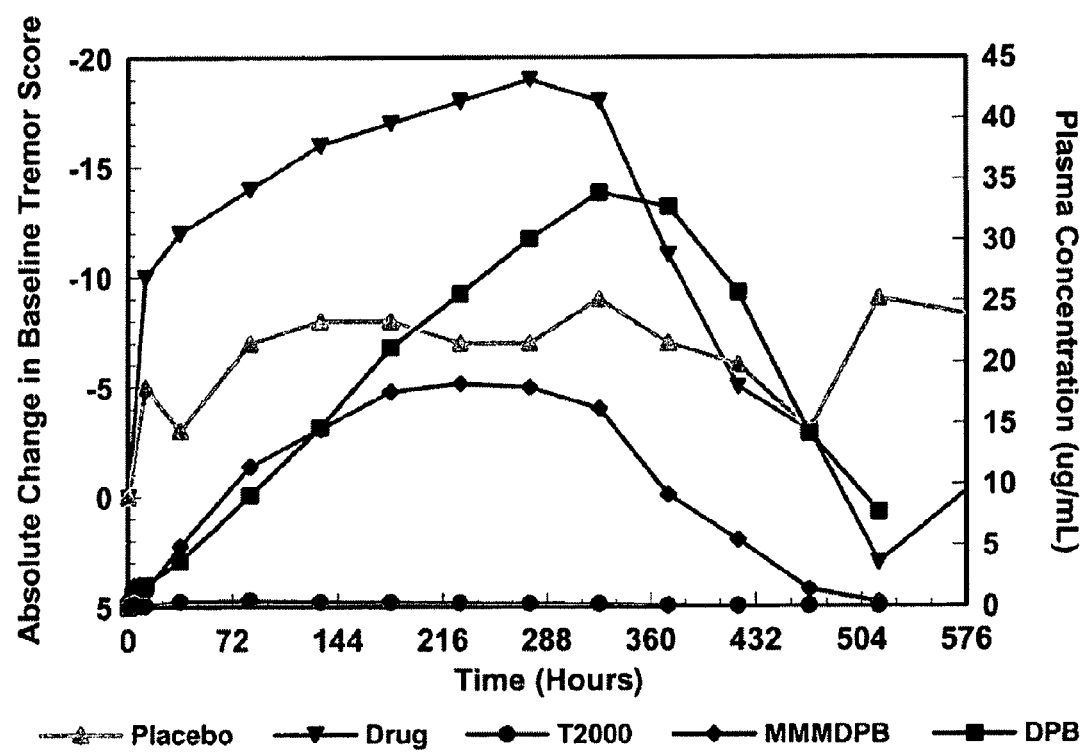
FIG. 1 shows the mean absolute change in baseline tremor score and plasma concentrations of DMMDBP, MMMDPB, and DPB after multiple oral doses of placebo or DMMDBP in patients with essential tremor, observed during the study set forth in Example 2.

In describing particular embodiments of the present invention, specific terminology is employed for the sake of clarity. However, the invention is not intended to be limited to the specific terminology so selected, and it is to be understood that each specific element includes all technical equivalents which operate in a similar manner to accomplish a similar purpose. Nevertheless, certain terms are given special definitions, as follows:

The term "combination" applied to active ingredients is used herein to define a single pharmaceutical composition (formulation) comprising at least two active ingredients or two or more separate pharmaceutical compositions (formulations), each comprising at least one active ingredient, said separate formulations to be administered conjointly.

The term "conjoint administration" and its variants (e.g., "administered conjointly") is used to refer to administration of two or more active ingredients simultaneously in one composition, or simultaneously in different compositions, or sequentially. For the sequential administration to be considered "conjoint," however, the active ingredients should be administered separated by no more than a time interval that still permits the resultant beneficial effect for treating, preventing, arresting, delaying the onset of and/or reducing the risk of developing a movement disorder. For example, the active ingredients should be administered on the same day (e.g., each—once or twice daily), preferably within an hour of each other, and most preferably simultaneously.

The term "treat" and its variants (e.g., "treatment", "treating") is used herein to mean to relieve, alleviate or eliminate at least one symptom of a disease in a subject. For example, in relation to tremor, the term "treat" means to reduce or to eliminate tremor or to decrease its intensity or to improve impairment of coordination associated with tremor. Such reduction or decrease should be measurable or perceptible to the physician attending the patient.

The present invention aims to provide a method for treating movement disorders such as essential tremor or Parkinson's disease. More specifically, it aims to treat movement disorders effectively and without the severe risks and/or side effects often associated with other treatment modalities, or with a significantly reduced number of such side effects and/or risks. Such risks and side effects include but are not limited to sedation, danger of overdose, and respiratory arrest.

Cyclic ureides having the following general formula (I):

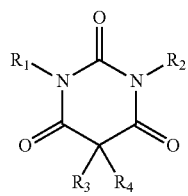

wherein $R_3$ and $R_4$ are each independently selected from the group consisting of lower alkyl, phenyl and lower alkyl substituted phenyl, and $R_1$ and $R_2$ are each independently either a hydrogen atom or a radical of the formula

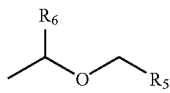

wherein $R_5$ and $R_6$ are each independently selected from the group consisting of H, lower alkyl, phenyl and lower alkyl substituted phenyl, its pharmaceutically acceptable salts, metabolites, and prodrugs thereof are useful in the treatment of movement disorders, especially essential tremor, tremor or other movement disorder associated with Parkinson's disease, focal dystonias, writer's cramp or restless leg syndrome or any of the other movement disorders enumerated above.

One preferred type of cyclic ureides useful in the method of the present invention are barbituric acid derivatives disubstituted at the 5-position. Another preferred embodiment of the present invention uses 5,5-diphenyl barbituric acid and derivatives for the treatment of movement disorders. Specific preferred compounds useful in the treatment method of the present invention include N,N-dimethoxymethyl diphenyl barbituric acid (DMMDPB), monomethoxymethyl diphenyl barbituric acid (MMMDPB) and diphenyl barbituric acid (DPB), and pharmaceutically acceptable salts and prodrugs thereof.

Compounds useful in the treatment method of the present invention can be made by any known synthetic technique. By way of illustration, U.S. Pat. Nos. 4,628,056 and 6,093,820, herein incorporated in their entirety by reference, disclose examples of such methods for the preparation of compounds used in the present invention. A preferred pathway for making MMMDPB is set forth in Example 1.

Compounds useful in the treatment method of the present invention may be formulated into compositions or formulations that additionally and optionally comprise any suitable adjuvants, excipients, additives, carriers, solvents, additional therapeutic agents (e.g., for conjoint use as a combination treatment, including for example one or more additional agents for combating the movement disorder and/or a concurrrent physiological condition), bioavailability enhancers, side-effect suppressing constituents, or other ingredients that do not adversely affect the efficacy of the composition for combating movement disorders.

Pharmaceutically acceptable salts of the movement disorder-combating compounds of the invention and physiologically functional derivatives thereof include salts derived from an appropriate base, such as an alkali metal (for example, sodium, potassium), an alkaline earth metal (for example, calcium, magnesium), ammonium and $NX_4^+$ (wherein X is $C_1$-$C_4$ alkyl). Pharmaceutically acceptable salts of an amino group include salts of organic carboxylic acids, such as tartaric, aliphatic, cycloaliphatic, aromatic, heterocyclic, carboxylic and sulfonic classes of organic acids, such as, for example, formic, glucuronic, malic, maleic, fumaric, pyruvic, aspartic, glutamic, benzoic, anthranilic, mesylic, salicylic, hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, hydroxybutyric, cyclochexylaminosulfonic, galactaric and galacturonic acid and the like, lactobionic, fumaric, and succinic acids; organic sulfonic acids, such as methaniesulfolic, ethanesulfonic, isothionic, benzenylesulfonic and p-toluenesulfonic acids; and inorganic acids such as hydrochloric, hydrobromic, hydroiodic, nitric, carbonic, sulfuric, sulfamic and phosphoric acid and the like. Pharmaceutically acceptable salts of a compound having a hydroxy group consist of the anion of said compound in combination with a suitable cation such as $Na^+$, $NH_4^+$ or $NX_4^+$ (wherein X is, for example, a $C_1$-$C_4$ alkyl group), $Ca^{++}$, $Li^+$, $Mg^{++}$, or, $K^+$ and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound in free form.

For use in treatments describes herein, salts of movement disorder-combating compounds of the invention will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention. Prodrugs and active metabolites of compounds disclosed herein are also within the scope of the invention.

Prodrugs

A prodrug is a pharmacologically active or more typically an inactive compound that is converted into a pharmacologically active agent by a metabolic transformation. In vivo, a prodrug readily undergoes chemical changes under physiological conditions (e.g., are acted on by naturally occurring enzyme(s)) resulting in liberation of the pharmacologically active agent. Prodrugs may be administered in the same manner as the active ingredient to which they convert or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

Suitable prodrugs of MMDPB include, but are not limited to, mono- and di-phosphate and mono and di-phosphonooxyalkyl derivatives of MMDPB. Preferred prodrugs are the mono- and di-phosphonooxymethyl derivatives.

An exemplary method for synthesis of the prodrugs involves a derivatizing agent represented by the formula shown below:

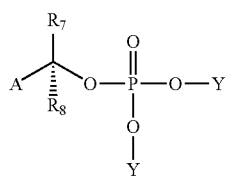
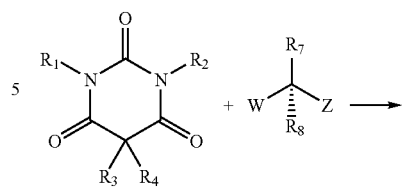

wherein A is any leaving group that is displaced by a nucleophilic tertiary amine group in the compounds of the present invention. Suitable examples of the leaving group A include, but are not limited to, tosylate, triflate, iodine, bromine, chlorine, acetate and hydroxyl. Further discussion of suitable leaving groups may be found in Hatshorn, S. R., Aliphatic Nucelophilic Substitution, Cambridge University Press, 1973.

$R_7$ and $R_8$ independently represent any suitable organic or inorganic residue, such as, but not limited to, straight chain or branched alkyl, such as methyl, ethyl, propyl, etc., an aromatic group, such as benzyl or phenyl, a cyclic hydrocarbon, such as cyclohexane, or any of the above substituted with one or more heteroatoms, such as S, N, or O.

Each Y independently represents a phosphate protecting group, such as, but not limited to, methyl, ethyl, tertiary butyl, benzyl, isopropyl, or more generally lower ($C_1$-$C_4$) alkyl or benzyl. Other suitable examples of phosphate protecting groups may be found in Green T. W., et al., Protective Groups In Organic Synthesis, 2nd Ed., Wiley, New York, 1991.

Synthesis of suitable prodrugs may be envisaged according to the scheme shown below:

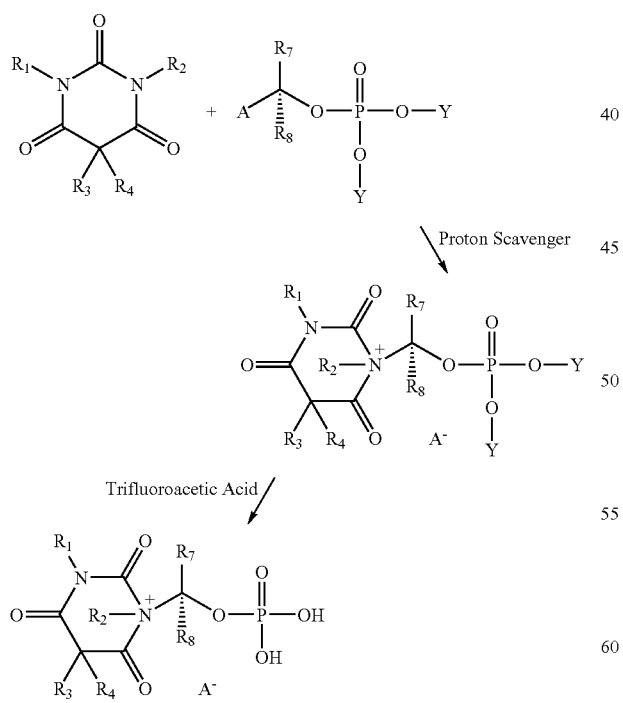

wherein $R_1$, $R_2$, $R_3$, and $R_4$ are as described above.

An alternate synthesis of the prodrugs is shown in the scheme below.

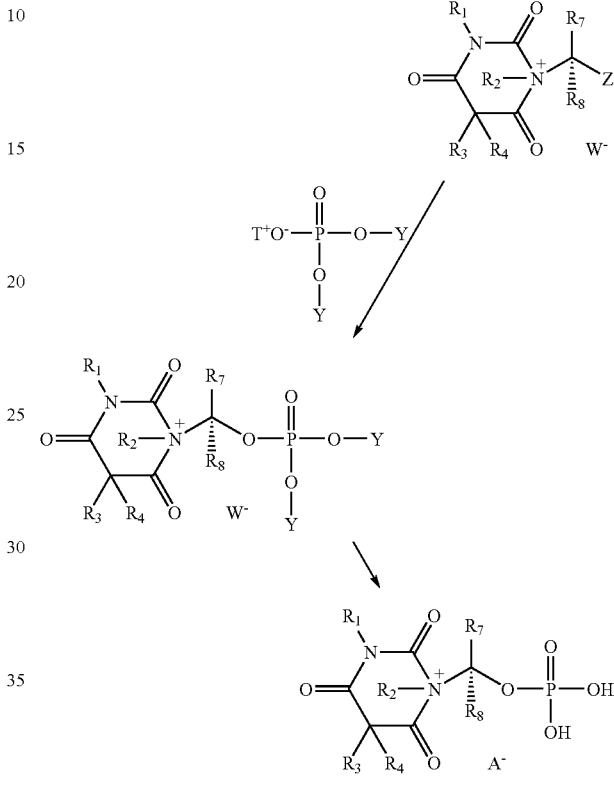

wherein W and Z are leaving groups similar to A, and can be the same or different. T is any organic or inorganic cationic species. Suitable reaction conditions for synthesis of the prodrugs are set forth in U.S. Pat. No. 5,985,856, which is hereby incorporated by reference in its entirety. The following are non-limiting examples of prodrugs specifically contemplated for use in present invention:

Formula (V)

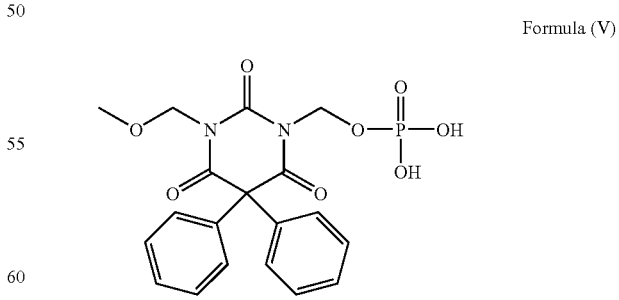

-continued

Formula (VI)

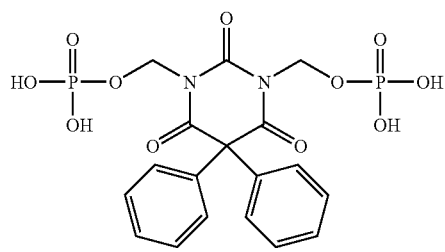

Formula (VII)

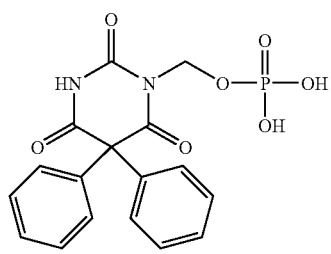

Additional prodrugs may readily be made by reacting a hydroxy derivative of one of the compounds of the present invention with an activated amino acyl, hemisuccinyl or acyl group to yield a prodrug ester. Alternatively, the hydroxy derivative can be reacted with halo alkyl esters or with bis alkanoyl acetals or condensed with acetic anhydride to yield additional prodrugs. See also U.S. Pat. Nos. 4,260,769 and 3,679,683, which are hereby incorporated by reference in their entireties.

Active Metabolites

An active metabolite is a compound which results from metabolism of another compound after administration of the latter to a subject. Metabolites can be identified by techniques well-known in the art. Examples of active metabolites are MMMDPB and DPB, each of which is generated in the recipient of DMMDPB. Conversely, each of MMMDPB and DMMDPB is a prodrug for DPB, and DMMDPB is a prodrug for MMNDPB.

The present invention also contemplates the treatment of movement disorders using pharmaceutical dosage forms containing at least one compound of the following formula:

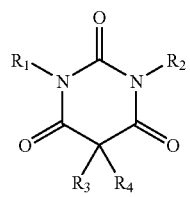

or a pharmaceutically acceptable salt, metabolite, or prodrug thereof, wherein $R_1$, $R_2$, $R_3$ and $R_4$ are as described, supra, both for veterinary and for human medical use.

In such pharmaceutical dosage forms, the active agent preferably is utilized together with one or more pharmaceutically acceptable carrier(s) therefore and optionally any other therapeutic ingredients. The carrier(s) must be pharmaceutically acceptable in the sense of being compatible with the other ingredients of the formulation and not unduly deleterious to the recipient thereof.

A subject in whom administration of the therapeutic compound is an effective therapeutic regimen for a disease or disorder is preferably a mammal, more preferably a human, but can be any animal, including a laboratory animal in the context of a clinical trial or screening or activity experiment employing an animal model. Thus, as can be readily appreciated by one of ordinary skill in the art, the methods and compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, research animals, such as mice, rats, rabbits, goats, sheep, pigs, dogs, cats, etc., avian species, such as chickens, turkeys, songbirds, etc., i.e., for veterinary medical use.

Depending on the specific movement disorder to be treated, a suitable therapeutically effective and safe dosage, as may readily be determined within the skill of the art, and without undue experimentation, maybe administered to subjects.

Effective Amounts

In general, while the effective dosage of compounds of the invention for therapeutic use in accordance with the inventions may be widely varied, depending on the specific application, movement disorder, or physiological state involved, as readily determinable within the skill of the art, suitable effective doses of the compounds and compositions described herein, and for achievement of a benefit in treatment, will broadly be in the range of 10 micrograms (μg) to 150 milligrams (mg) per kilogram body weight of the subject per day, preferably in the range of 50 μg to 130 mg per kilogram body weight per day, and most preferably in the range of 100 μg to 120 mg per kilogram body weight per day. The desired dose may be presented as one or more sub-doses) administered at appropriate intervals throughout the day, or alternatively in a single dose, preferably for morning or evening administration. These daily doses or sub-doses may be administered in unit dosage forms, for example, containing from about 150 mg to about 1500 mg, preferably from about 200 mg to about 1200 mg, more preferably from about 250 mg to about 850 mg, and most preferably about 450 mg of active ingredient per unit dosage form to be administered daily or twice daily. In specific embodiments, the daily dosage is equal to or greater than about 200, 250, 300, 350, 400, 450 mg of active ingredient per unit dosage form to be administered daily or twice daily. Typically, less than about 1500 mg of active ingredient of active ingredient per unit dosage form or preferably less than about 1200 mg is to be administered daily. Alternatively, if the condition of the recipient so requires, the doses may be administered as a continuous or pulsatile infusion. The duration of treatment may be decades, years, months, weeks, or days, as long as the benefits persist.

It is appreciated that the effective dose(s) may vary depending on the patient's age, sex, physical condition, duration and severity of symptoms, duration and severity of the underlying disease or disorder if any, and responsiveness to the administered compound. Accordingly, the foregoing ranges are guidelines and subject to optimization, and because of the good tolerability and low toxicity of the compounds of the present invention, higher doses may be administered. Effectiveness of a dose can be assessed using e.g., the criteria described in Fahn S. et al., Clinical rating scale for tremor, In: Parkinson's Disease and Movement Disorders, Jancovic J., Tolosa E. (Eds.) 1998 Urban & Swarzenberg, Inc. Baltimore, Md., USA 225-234, this section being incorporated by reference.

The mode of administration and dosage forms is closely related to the therapeutic amounts of the compounds or compositions which are desirable and efficacious for the given treatment application.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. Formulations suitable for oral administration are preferred.

To prepare such pharmaceutical dosage forms, one or more of the aforementioned compounds of formula (1) are intimately admixed with a pharmaceutical carrier according to conventional pharmaceutical compounding techniques. The carrier may take a wide variety of forms depending on the form of preparation desired for administration.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or delivery directly to the CNS. Administration may for example be intravenous, infra-arterial, intrathecal, intramuscular, subcutaneous, intramuscular, infra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The formulation of the present invention can have immediate release, sustained release, delayed-onset release or any other release profile known to one skilled in the art.

Pharmacokinetic studies of DMMDPB suggest that in humans the drug is rapidly metabolized to MMMDPB and then slowly metabolized to DPB. DBP has been shown to exert anticonvulsant properties in several animal models of seizure activity. (However, the present inventor has indications that in movement disorders MMMDPB may be active itself.) In any event, the administration of DMMDPB results in a sustained source of DPB, which has been shown to provide prolonged anticonvulsant activity.

DMMDPB, is a member of a class of nonsedating barbiturate compounds. It has been demonstrated in animal models to retain the anticonvulsant properties of phenobarbitol ('056 Patent). Thus, it offers the possibility of a broad spectrum, barbiturate anticonvulsant without the dose limiting side effect of sedation. By eliminating sedation, and thus increasing the tolerable dose, DMMDPB further offers the possibility of a more effective anticonvulsant by virtue of enabling the use of higher dosages. It is anticipated that these beneficial properties persist when this compound (or its metabolite e.g., MMMDPB and DPB) is used to treat movement disorders.

DMMDPB is a pro-drug and is converted to MMMDPB which in turn is converted to DPB, an active metabolite of DMMDPB. The latter conversion has been observed in both rats and dogs in addition to humans. DPB is a member of the barbituric class, which appears to possess anti-convulsant activity without the sedative hypnotic properties of some barbiturates. It has a shorter time course of action than DMMDPB. Pharmacokinetic studies in man indicate that DPB has an elimination half-life of the order of 55 hours, suggesting that DMMDPB could be administered once daily with a favorable impact on patient compliance. This information has relevance in the treatment of movement disorders.

There has been a substantial body of scientific work investigating the effect of DPB in animals. DPB exerts anti-convulsant properties in several animal models of seizure activity. The utilization of DMMDPB results in a sustained source of DPB, which provides prolonged anti-convulsant activity.

To assess safety in man and obtain pharmacokinetic information, a Phase I single dose study was performed in a total of 64 healthy male subjects. 48 subjects received DMMDPB and 16 subjects received placebo. All 64 subjects successfully completed the study. The subjects were healthy, non-smoking males between 18 and 55 years of age. The doses of DMMDPB administered orally in capsules were either 25 mg, 50 mg, 100 mg, 200 mg, 400 mg, 600 mg, 900 mg or 1200 mg under fed conditions (high fat breakfast).

DMMDPB, MMMDPB and DPB pharmacokinetics showed near linearity between administered dose and measured plasma levels up to 1200 mg. No neurological changes were observed. DMMDPB had no clear effect on cognitive or psychomotor functions with increasing dose.

A Phase I multiple dose clinical study was performed in a total of 40 healthy male subjects. 30 subjects received DMMDPB and 10 subjects received placebo. All 40 subjects successfully completed the study. The subjects were healthy, non-smoking males between 18 and 55 years of age. To each subject a total of 16 doses of DMMDPB were administered orally, a single dose in week one, followed by twice daily dosing for one week. Doses were either 150 mg, 200 mg, 300 mg, 450 mg or 600 mg under fed conditions.

DMMDPB was well tolerated. Minor adverse events were observed that also occurred with the placebo subjects. DMMDPB, MMMDPB and DPB pharmacokinetics showed near linearity up to 600 mg. Minimum plasma concentrations of DMMDPB, MMMPB and DPB on Days 13, 14 and 15 neurological changes were observed. DMMDPB had no clear effect on cognitive or psychomotor functions with increasing dose.

A Phase I clinical study was performed in a total of 16 healthy male subjects. 12 subjects received DMMDPB and 4 subjects received placebo. 15 subjects successfully completed the study. The subjects were healthy, non-smoking males between 18 and 55 years of age. A total of 28 doses of DMMDPB were administered orally, given twice daily for two weeks. Doses were either 450 mg or 600 mg under fed conditions.

DMMDPB was well tolerated. Minor adverse events were observed that also occurred with the placebo subjects. DMMDPB, MMMDPB and DPB pharmacokinetics showed near linearity up to 600 mg. Minimum plasma concentrations of DMMDPB, MMMPB and DPB on Days 13, 14 and 15 indicate that steady-state (DMMDPB, MMMDPB) and near steady-state (DPB) was achieved with 14 days of dosing (28 doses). No neurological changes were observed. DMMDPB had little or no effect on cognitive or psychomotor functions.

It is expected that treatment with non-sedating barbiturates may be effective for therapy in controlling all movement disorders. Specifically, stimulation of the ventral intermediate nucleus of the thalamus appears to be very effective in the treatment of tremor, not only in patients having Parkinson's disease but also in patients with essential tremor. Lozano. Arch. Med. Res. 2000, 31(3):266-269; Kiss et al., Neuroscience, 2002, 113(1):137-143. Stereotactic thalamotomy has been used in selective cases to treat Parkinson's disease as well as essential tremor. Balas et al., Rev. Neruol. 2001, 32(6):520-524. These findings suggest that the neurologic substrate necessary for the generation of tremor in Parkinson's disease and essential tremor may be similar, and the present inventor fully anticipates them to respond to the same treatment. Moreover, the observational evidence adduced by the present inventor that the present treatment is effective for focal dystonias, such as writer's cramp, supports the notion that the present invention is effective for the treatment of all movement disorders, whether associated with a disease such as Parkinson's or essential tremor, or one of unknown, or idiopathic origin.

EXAMPLES

The features and advantages of the invention are more fully shown by the following non-limiting examples.

Example 1

Synthesis of MMMDPB

A reactor was charged with chlorobenzene (15 ml), and stirring and an $N_2$ flow were started. N,N-bismethoxymethyl barbituric acid (1.84 g) was added to the reactor. The mixture was stirred for 10 minutes and then heated up to 55-60° C. The mixture was stirred for another 10 minutes. Aluminum chloride (AICl3, 0.66 g) was added. The mixture was stirred for 10 minutes at about 60° C. The mixture was heated up to 100-110° C. and stirred for another 10 minutes. The mixture was cooled to 60° C. The $N_2$ flow was stopped. A cold solution of hydrochloric acid (32%, 0.5 ml) in deionized water (30 ml) was added. The mixture was stirred at 5° C. for about 30 minutes. The suspension was filtered, and the filter cake was washed with cold chlorobenzene (2 ml). The filtrate from the washing was added to the filtrate from the filtration. The chlorobenzene (lower) phase was separated. The majority of chlorobenzene from the lower phase was allowed to evaporate. The resulting residue was diluted with ethyl acetate (10 ml). The solution was extracted with 0.5 N sodium hydroxide (15 ml), while maintaining the temperature of the solution at 20° C. or lower. The ethyl acetate phase was washed with cold deionized water (15 ml). Water was added to the basic extract. The extract was acidified with a hydrochloric acid solution (32%, 1 ml), while maintaining its temperature below 20° C. The mixture was stirred for 30 minutes. The suspension was then filtered. The filter cake was washed with deionized water (5 ml) to yield crude MMMDPB.

The crude product was purified as follows. A second reactor was charged with ethanol (95%, 4.5 ml). Stirring was started. The crude MIVIMDPB (0.87 g) was added to the reactor. The mixture was heated up to 60° C. and stirred for about 30 minutes. The mixture was cooled to room temperature and stirred for about 30 minutes. The resulting suspension was filtered. The filter cake was washed with ethanol (95%, 1 ml). The wet product was dried in a vacuum oven at 60° C. for about 10 hours.

Example 2

Treatment of Essential Tremor in a Phase II Double-Blind Study

Twelve patients were selected using criteria for definite essential tremor as classified by the National Institute of Health (NIH) Diagnostic Criteria for Essential Tremor and the Tremor Investigation Group (TRIG) Proposed Criteria for Diagnosing Essential Tremor. See Jankovic J. Essential Tremor: Clinical Characteristics, Neurology, 20000:54 (Suppl 4); S21-25, incorporated by reference in its entirety. According to these protocols, patients must have bilateral postural tremor of both upper extremities with an amplitude rating of 2 or greater in one arm and 1 or greater in the other, which is visible, persistent, and longstanding (preferably >3 years). Patients were tapered off medications and vitamins, energy drinks, grapefruit and supplements 7 days prior to the commencement of the study. They were instructed to stop tremor medications 14 days prior to study commencement, after taper. There were some dietary restrictions:

The patients were randomized to receive with DMMDPB, 400 mg twice daily in the morning and evening (12 hours apart, total daily dose 800 mg) or placebo (9 patients on drugs, 3 on placebo) for 14 days. Patients were confined one day prior to dosing and for the initial two days of dosing for the baseline neurological assessment. Evaluations of tremor were conducted on days 0, 1, 2, 4, 6, 8, 10, 12, 14, 15, 16, 18, 20 and at least 2 weeks after termination of treatment using established rating methods. See Fahn S. et al., Clinical rating scale for tremor, In: Parkinson's Disease and Movement Disorders, Jancovic J., Tolosa E. (Eds.) 1998 Urban & Swarzenberg, Inc. Baltimore, Md., USA 225-34. Concurrent plasma concentrations of DMMDPB were measured. Blood samples were collected on days 1, 2, 4, 6, 8, 10, 12, 14 and during morning visits on days 16, 18, 20, 22 and at 2, 4, 8 and 12 hours past the trial administration. Adverse events were also assessed.

Evaluations of tremor were conducted with at least one of a clinical rating scale, a patient-reported disability/symptom scale, and neurophysiological measurements, such as accelerometric recordings. Since the correlation between accelerometry scores and functional disability scores has been subject to criticism in the literature, clinical grading scales and patient reporting were used as the primary parameters.

On unblinding, patients 2-4, 6-9 and 11 were treated and patients 1, 5 and 10 were on placebo. As can be seen from Table 1, five of the nine treated patients showed improvement greater than 50% compared to baseline after treatment with DMVMBP for 14 days. Placebo patients exhibited less than 50% improvement. The level of improvement shown in the drug-treated patients was statistically significant (p<0.02) by one-tail t test.

The mean absolute change in baseline tremor score and plasma concentrations of DMMDBP, MMMDPB, and DPB is shown in Table 2, and FIG. 1.

TABLE 2

| Time | | Absolute Change in Baseline Tremor | | Plasma Concentration (µg/ml) | | |
|---|---|---|---|---|---|---|
| Days | Hours | Placebo | Drug | DMMDPB | MMMDPB | DPB |
| 1 | 0 | 0 | 0 | 0.00 | 0.00 | 0.00 |
| 1 | 1 | ND | ND | 0.03 | 0.21 | 0.11 |
| 1 | 2 | ND | ND | 0.19 | 0.71 | 0.29 |
| 1 | 4 | ND | ND | 0.33 | 1.73 | 0.97 |
| 1 | 8 | ND | ND | 0.11 | 1.27 | 1.44 |
| 1 | 12 | −5 | −10 | 0.10 | 1.22 | 1.78 |
| 2 | 36 | −3 | −12 | 0.42 | 4.96 | 3.72 |
| 4 | 84 | −7 | −14 | 0.50 | 11.50 | 9.11 |
| 6 | 132 | −8 | −16 | 0.37 | 14.54 | 14.67 |
| 8 | 180 | −8 | −17 | 0.33 | 17.61 | 21.23 |
| 10 | 228 | −7 | −18 | 0.27 | 18.27 | 25.62 |
| 12 | 276 | −7 | −19 | 0.22 | 17.96 | 30.13 |
| 14 | 324 | −9 | −18 | 0.19 | 16.21 | 33.90 |
| 16 | 372 | −7 | −11 | 0.07 | 9.12 | 32.74 |
| 18 | 420 | −6 | −5 | 0.03 | 5.43 | 25.70 |
| 20 | 468 | −3 | −3 | 0.03 | 1.37 | 14.13 |
| 22 | 516 | −9 | −3 | 0.02 | 0.31 | 7.68 |
| 24 | −684 | −7 | −6 | ND | ND | ND |

ND = Not Determined

Figure 2:
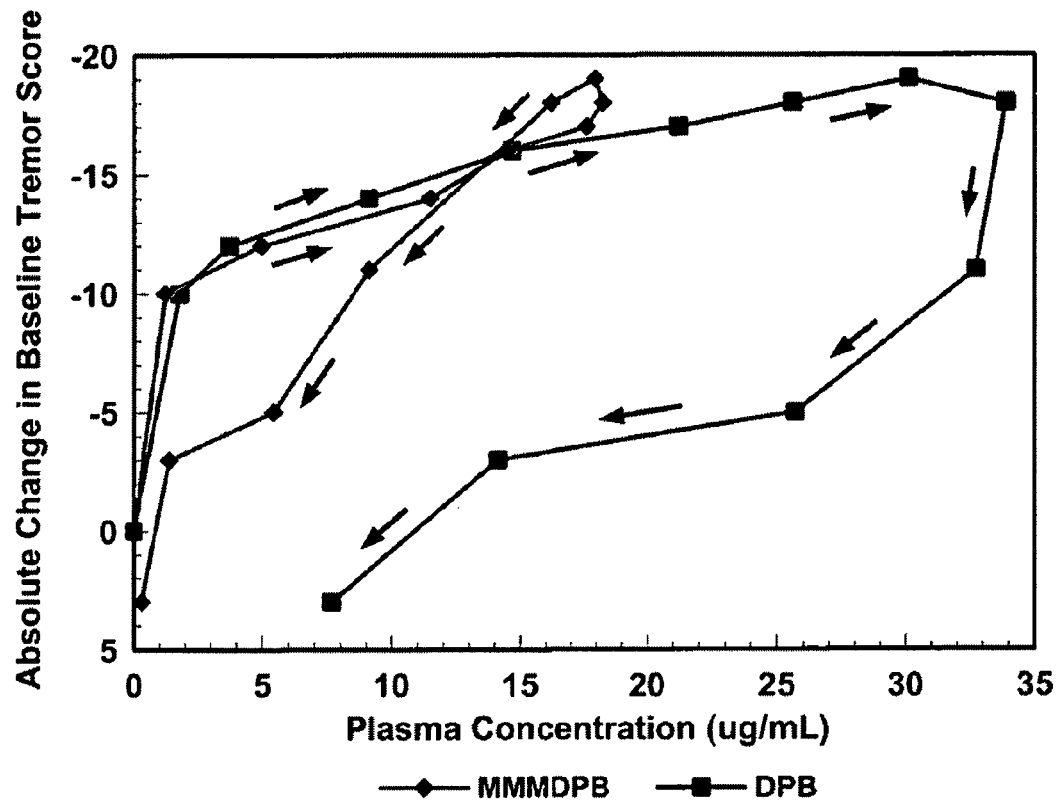
FIG. 2 shows the mean absolute change in baseline tremor score vs. plasma concentrations of MMMDPB and DPB after multiple oral doses of DMMDPB in patients with essential tremor, observed during the study set forth in Example 2.

The mean absolute change in baseline tremor score vs. plasma concentrations of MMDPB and DPB after multiple oral doses of DMMDPB in patients with essential tremor is shown in FIG. 2.

Table 3 shows a comparison of the mean change in tremor score from baseline (Day-1) to a composite endpoint (average of Days 12 and 14) between those patients treated with the drug (DMMDBP) and those treated with a placebo. The mean absolute change in the treated group was 18.3 as compared to 8.0 in the placebo group. This difference is statistically significant using a 2-tailed Student's t-test for independent groups (p=0.05).

TABLE 1

| | Drug Response | | | (C − B) | | (D − B) | | (D − C) | |
|---|---|---|---|---|---|---|---|---|---|
| Subject# | Baseline Score "B" | Avg. of days/1, 2, 4 | Avg. of days 6, 8, 10, 12, 14 | Absolute First Period | First Period % | Overall Change @ 14 | Overall % Change | Second Period Difference | Second Period % |
| 9 | 31.0 | 11.3 | 6.8 | 19.7 | −64% | 24.2 | −78% | 4.5 | −40% |
| 3 | 33.0 | 15.7 | 9.5 | 17.3 | −52% | 23.5 | −71% | 6.2 | −39% |
| 7 | 20.0 | 10.7 | 6.2 | 9.3 | −47% | 13.8 | −69% | 4.5 | −42% |
| 4 | 25.0 | 18.3 | 15.2 | 6.7 | −27% | 9.8 | −39% | 3.1 | −17% |
| 6 | 17.0 | 10.7 | 9.8 | 6.3 | −37% | 7.2 | −42% | 0.9 | −8% |
| 11 | 16.0 | 9.7 | 9.2 | 6.3 | −39% | 6.8 | −43% | 0.5 | −5% |
| 8 | 21.0 | 15.0 | 9.2 | 6.0 | −29% | 11.8 | −56% | 5.8 | −39% |
| 2 | 24.0 | 18.7 | 11.8 | 5.3 | −22% | 12.2 | −51% | 6.9 | −37% |
| 10 | 14.0 | 9.0 | 8.0 | (5.0) | −36% | (6.0) | −43% | (1.0) | −11% |
| 1 | 17.0 | 14.0 | 13.8 | (3.0) | −18% | (3.2) | −19% | (0.2) | −1% |
| 12 | 22.0 | 19.0 | 13.8 | 3.0 | −14% | 8.2 | −37% | 5.2 | −27% |
| 5 | 22.0 | 20.7 | 13.8 | (1.3) | −6% | (8.2) | −37% | (6.9) | −33% |

TABLE 3

| Treatment | N | Baseline Tremor Score (Day −1) | Absolute Change From Baseline Tremor Score (Day −1) | P Value[1] |
|---|---|---|---|---|
| Placebo | 3 | 25.0 | −8.0 | 0.05 |
| Drug | 8 | 32.0 | −18.3 | |

N is the number of patients in the group.
[1]Patient's t-test, treated vs. placebo, 2-tailed Table 4 shows a comparison of the linear trends in tremor score from baseline (Day 0) to a single endpoint (Day 14) between the group of patients treated with the drug (DM-MDBP) and the group of patients given a placebo. All the data points between Day 0 and Day 14 were used in this analysis. The respective baseline and Day 14 performance scores were 32.0 and 13.9 in the treated group as compared to 25.0 and 16.0 in the placebo group. The treated and placebo performance score linear trends from Day 0 to Day 14 were found to differ significantly using a 2-factor mixed ANOVA model followed by a 1-tailed F-test for comparison of linear trends (P=0.05). In using this repeated measures statistical approach, the linear trends were observed within subject, with between subject effects being filtered out.

TABLE 4

| Treatment | N | Baseline Tremor Score (Day −1) | Absolute Change From Baseline Tremor Score (Day −1) | P Value[1] |
|---|---|---|---|---|
| Placebo | 3 | 25.0 | 16.0 | 0.05 |
| Drug | 8 | 32.0 | 13.9 | |

N is the number of patients in that treatment group.
[1]Difference in linear trend, treated vs. placebo, 1-tailed.

Example 3

Treatment of Parkinson's Disease

Patients with treated, symptomatic Parkinson's disease are often troubled by tremor, by dystonia and chorea movements (dyskinesias) secondary to dopaminergic agents and by prominent motor fluctuations throughout the day ("'wearing-off' or "on-off"). In addition, Parkinson's disease may sometimes have some intrinsic dystonic features. All of these tremor features may potentially be alleviated by treatment with T2000 or related compounds.

We will select 25 patients having on-off phenomena and 25 patients with tremor (the two groups may partially overlap, i.e., some patients may exhibit both syndromes). These patients will be treated with from 400 up to 800 mg of DMMDPB orally each day for two to three weeks. Patients will be monitored every other day to evaluate the degree of reduction in tremor and time in the "off" state as indicated using a modification of the Unified Parkinson's Disease Rating Scale (UPDRS). Koller, W. C., and Tolosa, E., Current and Emerging Drug Therapies in the Management of Parkinson's Disease, 50(6): S1-S48 (1998). It is anticipated that after two weeks of treatment, the treated patients will show a 25-50% reduction in tremor and a greater than about 10% in the time-off state as evidenced by routine neurologic examination.

Improvement in dyskinesia (dystonia and chorea) will also be assessed. Preliminary observations indicate that dystonic symptoms (e.g., writer's cramp) in patients with essential tremor are alleviated by therapy using 450 mg per day of DMMDPB to treat tremor. It is thus anticipated that the aforementioned regime will show effectiveness in dystonia and more generally dyskinesia of patients with Parkinson's disease.

Example 4

Treatment of Essential Tremor with a Phosphonooxymethyl Derivative

Twenty patients will be selected using criteria for definite essential tremor as classified by the National Institute of Health (NIH) Diagnostic Criteria for Essential Tremor and the Tremor Investigation Group (TRIG) Proposed Criteria for Diagnosing Essential Tremor. See Jankovic J. Essential Tremor: Clinical Characteristics, Neurology, 20000:54 (Suppl4); S21-25, incorporated by reference in its entirety. According to these protocols, patients must have bilateral postural tremor of both upper extremities with an amplitude rating of 2 or greater in one arm and 1 or greater in the other, which is visible, persistent, and longstanding (preferably >3 years). Patients will be tapered off medications and vitamins, energy drinks, grapefruit and supplements 7 days prior to the commencement of the study. They will be instructed to stop tremor medications 14 days prior to study commencement, after taper.

The patients will be randomized to receive phosphonooxymethyl derivatives, 400 mg twice daily in the morning and evening (12 hours apart, total daily dose 800 mg) or placebo (9 patients on drugs, 3 on placebo) for 14 days. Patients will be confined one day prior to dosing and for the initial two days of dosing for the baseline neurological assessment. Evaluations of tremor will be conducted on days 0, 1, 2, 4, 6, 8, 10, 12, 14, 15, 16, 18, 20 and at least 2 weeks after termination of treatment using established rating methods. See Fahn S. et al., Clinical rating scale for tremor, In: Parkinson's Disease and Movement Disorders, Jancovic J., Tolosa E. (Eds.) 1998 Urban & Swarzenberg, Inc. Baltimore, Md., USA 225-34. Concurrent plasma concentrations of phosphonooxymethyl derivatives, MMMDPB and DPB will be measured. Blood samples will be collected on days 1, 2, 4, 6, 8, 10, 12, 14 and during morning visits on days 16, 18, 20, 22 and at 2, 4, 8 and 12 hours past the trial administration.

Evaluations of tremor will be conducted with at least one of a clinical rating scale, a patient-reported disability/symptom scale, and neurophysiological measurements, such as accelerometric recordings. Since the correlation between accelerometry scores and functional disability scores has been subject to criticism in the literature, clinical grading scales and patient reporting will be used as the primary parameters.

On unblinding, we expect that patients treated with phosphonooxymethyl derivatives will have shown a significantly decreased tremor as opposed to patients treated with placebo.

The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

All patents, applications, publications, test methods, literature, and other materials cited herein are hereby incorporated by reference.

The invention claimed is:

1. A method of treating movement disorders comprising administering to a subject in need of treatment, a composition comprising an effective amount of a compound selected from the group consisting of N,N-dimethoxymethyl-5,5-diphenylbarbituric acid, N-methoxymethyl-5,5-diphenylbarbituric acid, and 5,5-diphenylbarbituric acid, or a pharmaceutically acceptable salt thereof, wherein said movement disorder is selected from the group consisting of Parkinson's disease, essential tremor, focal dystonias, and restless leg syndrome.

2. The method of claim 1 wherein the focal dystonia is selected from the group consisting of writer's cramp and torticollis.

3. The method of claim 1 wherein the composition comprises N,N-dimethoxymethyl-5,5-diphenylbarbituric acid.

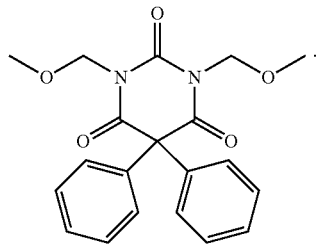

4. The method of claim 1 wherein the composition comprises N-methoxymethyl-5,5-diphenylbarbituric acid

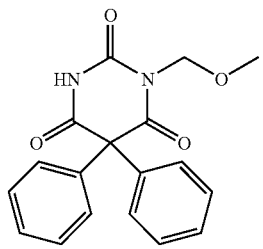

or a pharmaceutically acceptable salt thereof.

5. The method of claim 4, wherein the composition comprises a pharmaceutically acceptable salt of the compound.

6. The method of claim 5, wherein the pharmaceutically acceptable salt comprises a sodium salt.

7. The method of claim 1, wherein the composition comprises 5,5-diphenylbarbituric acid

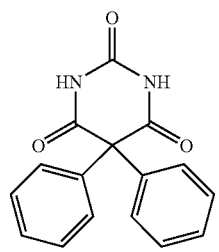

or a pharmaceutically acceptable salt thereof.

8. The method of claim 3 wherein the focal dystonia is selected from the group consisting of writer's cramp and torticollis.

9. The method of claim 4 wherein the focal dystonia is selected from the group consisting of writer's cramp and torticollis.

10. The method of claim 7 wherein the focal dystonia is selected from the group consisting of writer's cramp and torticollis.

11. A method of treating movement disorders comprising administering to a subject in need of treatment, a composition comprising an effective amount of a compound according to the following formula:

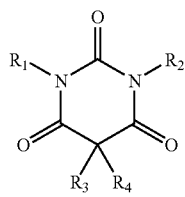

or a pharmaceutically acceptable salt, thereof, wherein $R_3$ and $R_4$ are each independently selected from the group consisting of phenyl and lower alkyl substituted phenyl, and $R_1$ and $R_2$ are each independently either a hydrogen atom or a radical of the formula

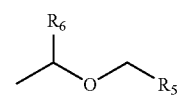

Wherein $R_5$ and $R_6$ are each independently selected from the group consisting of H, lower alkyl, phenyl, and lower alkyl substituted phenyl.

12. The method of claim 11, wherein the movement disorder is selected from the group consisting of essential tremor, dystonia, chorea, athetosis, a tic disorder, blepharospasm, hemiballysmus, myoclonus, toricollis, writer's cramp, restless leg syndrome, asterixis, Parkinson's disease, Tourette's syndrome, progressive supranuclear palsy, and Wilson's disease.

13. The method of claim 12, wherein the movement disorder is selected from the group consisting of Parkinson's disease, essential tremor, focal dystonias, and restless leg syndrome.

14. The method of claim 13, wherein the focal dystonia is selected from the group consisting of writer's cramp and torticollis.

15. The method of claim 11 wherein the compound is selected from the group consisting of N,N-dimethoxymethyl-5,5-diphenylbarbituric acid, N-methoxymethyl-5,5-diphenylbarbituric acid, and 5,5-diphenylbarbituric acid, or a pharmaceutically acceptable salt thereof.

16. The method of claim 15 wherein the compound is N,N-dimethoxymethyl-5,5-diphenylbarbituric acid.

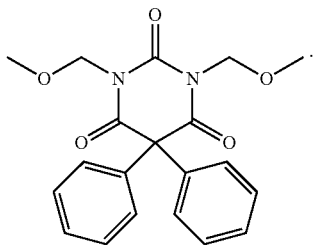

17. The method of claim 15 wherein the compound is N-methoxymethyl-5,5-diphenylbarbituric acid

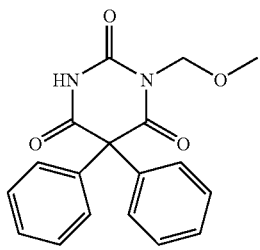

or a pharmaceutically acceptable salt thereof.

18. The method of claim 17, wherein the compound comprises a pharmaceutically acceptable salt.
19. The method of claim 18, wherein the pharmaceutically acceptable salt comprises a sodium salt.
20. The method of claim 15, wherein the compound is 5,5-diphenylbarbituric acid

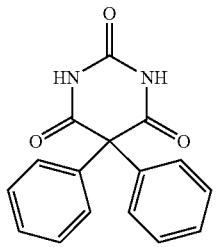

or a pharmaceutically acceptable salt thereof.
21. The method of claim 20, wherein the compound comprises a pharmaceutically acceptable salt.
22. The method of claim 21, wherein the pharmaceutically acceptable salt comprises a sodium salt.

* * * * *